US009764041B2

(12) United States Patent
Ishii et al.

(10) Patent No.: US 9,764,041 B2
(45) Date of Patent: *Sep. 19, 2017

(54) DRUG CONJUGATE COMPRISING ANTI-CDH3 (P-CADHERIN) ANTIBODY

(75) Inventors: Keisuke Ishii, Tokyo (JP); Katsuyuki Mitomo, Tokyo (JP); Katsushi Kouda, Tokyo (JP); Fumiko Nomura, Tokyo (JP); Yoko Kayukawa, Tokyo (JP); Tadashi Matsuura, Tokyo (JP)

(73) Assignee: PERSEUS PROTEOMICS INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/390,734

(22) PCT Filed: Apr. 4, 2012

(86) PCT No.: PCT/JP2012/059236
§ 371 (c)(1),
(2), (4) Date: Oct. 3, 2014

(87) PCT Pub. No.: WO2013/150623
PCT Pub. Date: Oct. 10, 2013

(65) Prior Publication Data
US 2016/0058883 A1 Mar. 3, 2016

(51) Int. Cl.
*A61K 39/395* (2006.01)
*A61K 47/48* (2006.01)
*C07K 16/28* (2006.01)
*C07K 16/30* (2006.01)

(52) U.S. Cl.
CPC .. *A61K 47/48569* (2013.01); *A61K 47/48584* (2013.01); *A61K 47/48676* (2013.01); *A61K 47/48715* (2013.01); *C07K 16/28* (2013.01); *C07K 16/30* (2013.01); *C07K 16/3015* (2013.01); *C07K 2317/565* (2013.01)

(58) Field of Classification Search
None
See application file for complete search history.

(56) References Cited

U.S. PATENT DOCUMENTS

| 8,088,387 B2 | 1/2012 | Steeves et al. | |
| 8,435,749 B2* | 5/2013 | Togashi | 424/130.1 |
| 9,017,669 B2* | 4/2015 | Shiba | A61K 51/1027 |
| | | | 424/130.1 |
| 9,328,160 B2* | 5/2016 | Ishii | C07K 16/18 |
| 2007/0048314 A1* | 3/2007 | Dai | A61K 47/48407 |
| | | | 424/145.1 |
| 2012/0128584 A1 | 5/2012 | Togashi et al. | |
| 2012/0238731 A1* | 9/2012 | Fishkin | A61K 47/48215 |
| | | | 530/391.9 |
| 2012/0251558 A1* | 10/2012 | Gerber | A61K 47/48384 |
| | | | 424/181.1 |

FOREIGN PATENT DOCUMENTS

| CA | 2 789 310 A1 | 8/2011 |
| CN | 101432303 A | 5/2009 |
| CN | 101573384 A | 11/2009 |
| CN | 102137929 A | 7/2011 |
| EP | 2 634 194 A1 | 9/2013 |
| JP | 2004-520450 A | 7/2004 |
| JP | 2009-528257 A | 8/2009 |
| JP | 2010-523469 A | 7/2010 |
| WO | WO 02/097395 A2 | 12/2002 |
| WO | WO 02/098883 A1 | 12/2002 |
| WO | WO 2007/102525 A1 | 9/2007 |
| WO | WO 2008/052187 A2 | 5/2008 |
| WO | 2010/001585 * | 1/2010 |
| WO | WO 2011/080796 A1 | 7/2011 |

OTHER PUBLICATIONS

Brown et al (J. Immunol. May 1996; 156(9):3285-3291.*
Vajdos et al (J. Mol. Biol., Jul. 5, 2002;320(2); 415-428).*
Chinese Office Action dated Aug. 20, 2015, issued in corresponding Chinese Patent Application No. 201280072237.X.
Chikako Yoshida et al.; Teratocarcinoma Cell Adhesion: Identification of a Cell-Surface Protein Involved in Calcium-Dependent Call Aggregation; Cell; vol. 28; pp. 217-224; 1982.
International Preliminary Report on Patentability dated Oct. 16, 2014, issued in PCT/JP2012/059236 (Forms PCT/IB/338, PCT/IB/373, PCT/IB/237 and PCT/IB/326).
International Search Report dated Jun. 19, 2012, issued in PCT/JP/2012/059236 (Form PCT/ISA/210).
Chinese Office Action and Chinese Search Report, issued Apr. 22, 2016, for Chinese Application No. 201280072237.X, along with English translations.
Supplementary European Search Report issued Dec. 22, 2015, in European Patent Application No. 12873679.0.
Japanese Office Action and English excerpt dated Feb. 2, 2016 for corresponding Application No. 2014-508962.
Henry et al., "A Prostate-Specific Membrane Antigen-Targeted Monoclonal Antibody-Chemotherapeutic Conjugate Designed for the Treatment of Prostate Cancer," Cancer Research, vol. 64, Nov. 1, 2004, pp. 7995-8001.
Japanese Office Action, dated Oct. 11, 2016, for Japanese Application No. 2014-508962, together with an English translation thereof.
Mackay et al., "cDNA microarray analysis of genes associated with ERBB2 (HER2/neu) overexpression in human mammary luminal epithelial cells," Oncogene, vol. 22, 2003, pp. 2680-2688.
Oroudjev et al., "Maytansinoid-Antibody Conjugates Induce Mitotic Arrest by Suppressing Microtubule Dynamic Instability," Molecular Cancer Therapeutics, vol. 9, No. 10, Oct. 2010, pp. 2700-2713.

(Continued)

*Primary Examiner* — Sheela J Huff
(74) *Attorney, Agent, or Firm* — Birch, Stewart, Kolasch & Birch, LLP

(57) ABSTRACT

It is an object of the present invention to provide a drug conjugate comprising an anti-CDH3 antibody that efficiently kills cancer cells expressing CDH3. According to the present invention, there is provided an immune complex formed by binding an antibody against CDH3 or a fragment thereof having CDH3 binding ability to a chemotherapeutic agent.

15 Claims, 5 Drawing Sheets

(56) References Cited

OTHER PUBLICATIONS

Polson et al., "Anti-CD22-MCC-DM1: an antibody-drug conjugate with a stable linker for the treatment of non-Hodgkin's lymphoma," Leukemia, vol. 24, 2010 (published online Jul. 1, 2010), pp. 1566-1573.
Zhou et al., "Internalizing Cancer Antibodies from Phage Libraries Selected on Tumor Cells and Yeast-Displayed Tumor Antigens," Journal of Molecular Biology, vol. 404, 2010 (available online Sep. 17, 2010), pp. 88-99.
Chinese Office Action issued in Chinese Patent Application No. 201280072237.X on Jan. 6, 2017.

\* cited by examiner

[Figure 1]
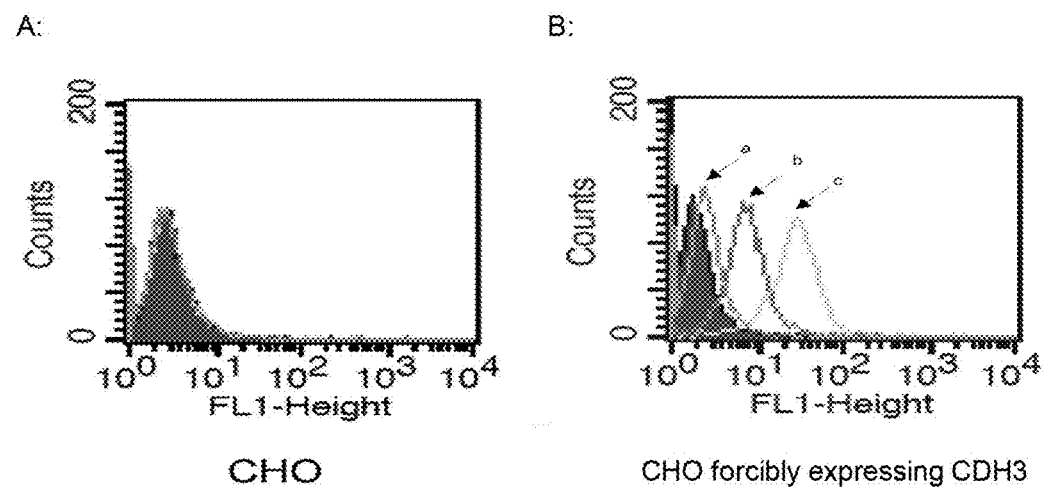
[Figure 2]
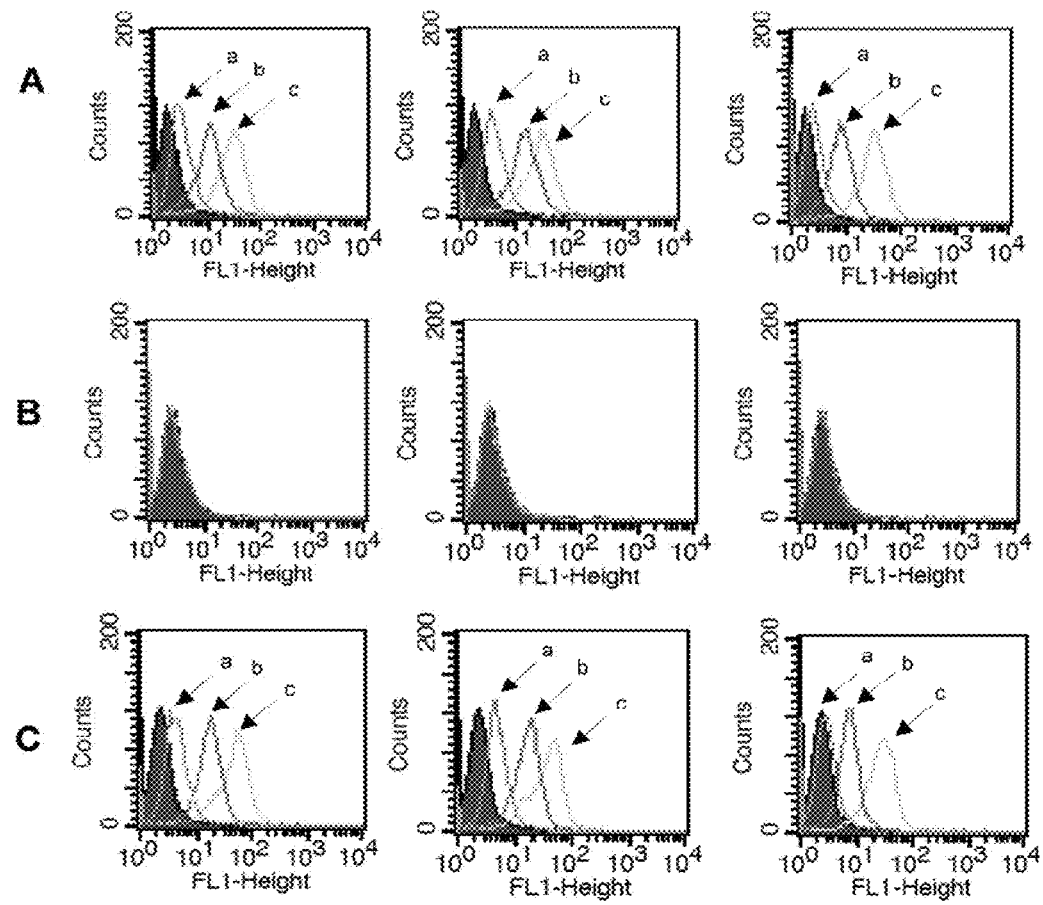

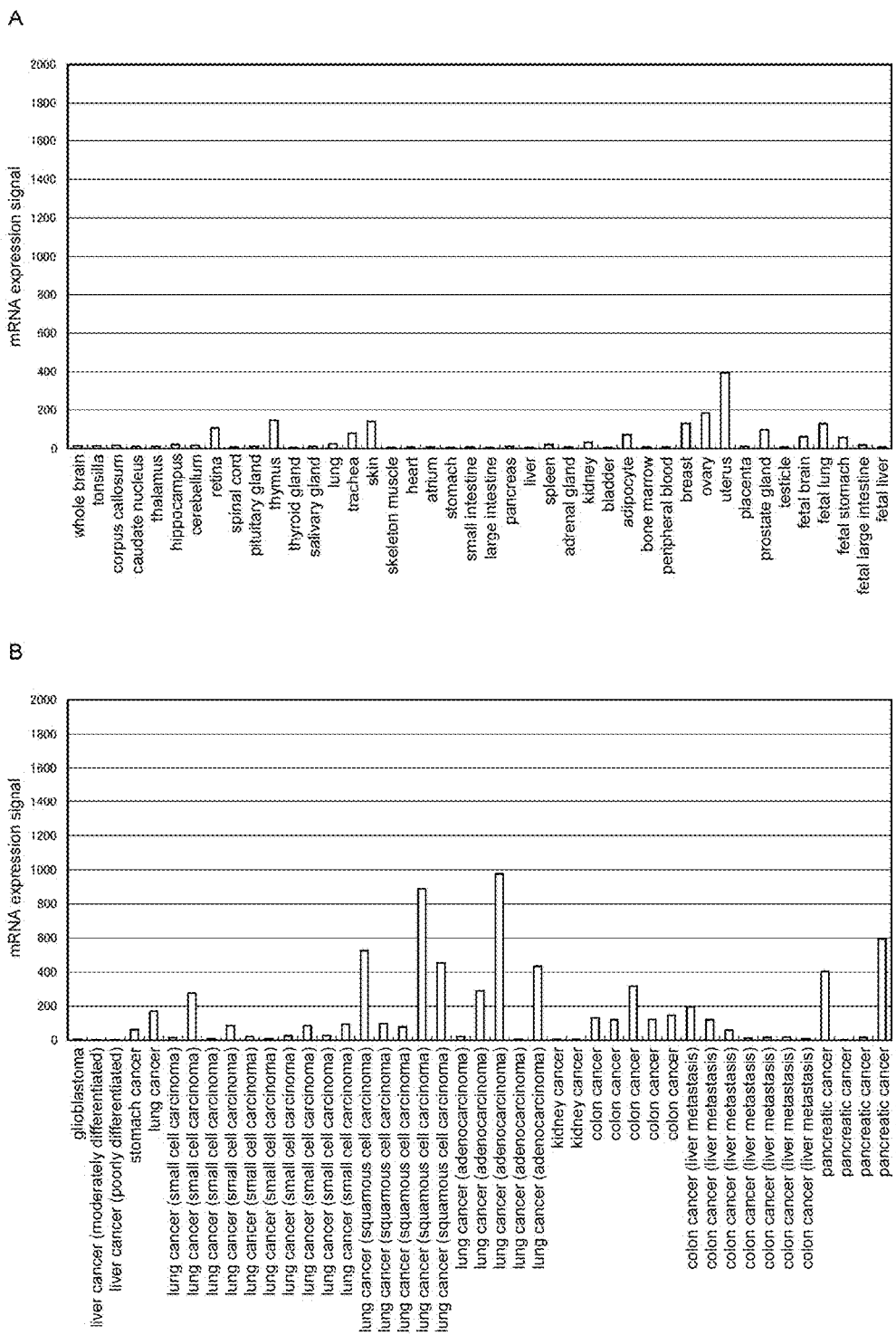
[Figure 3]

[Figure 3]
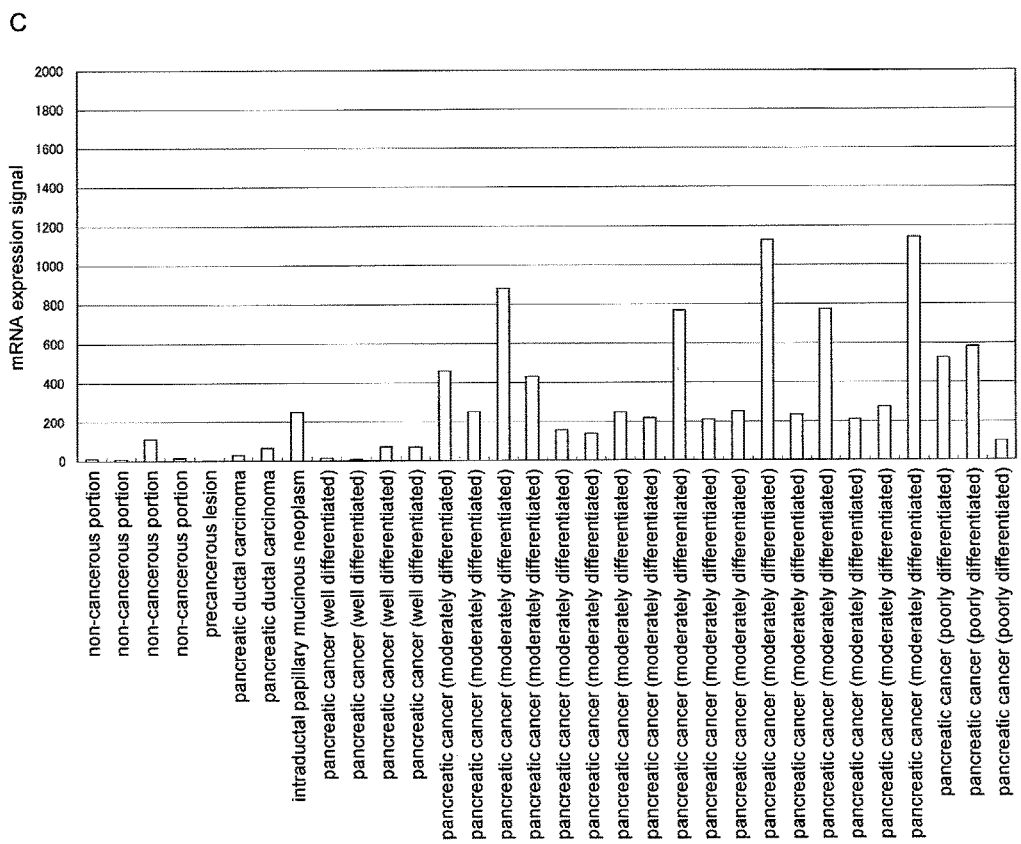

[Figure 4]
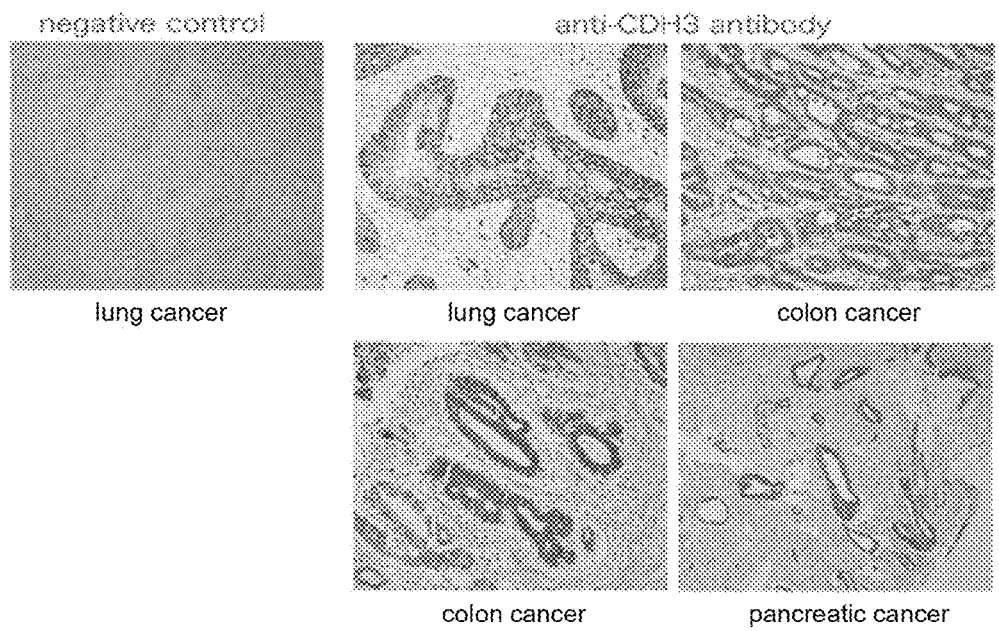
[Figure 5]
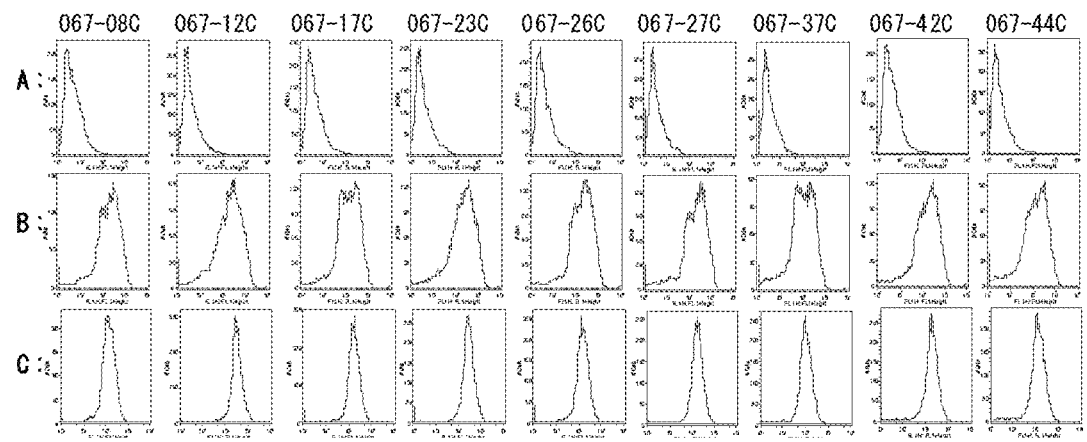
[Figure 6]
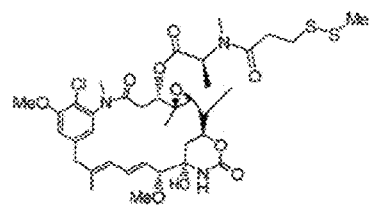

[Figure 7]
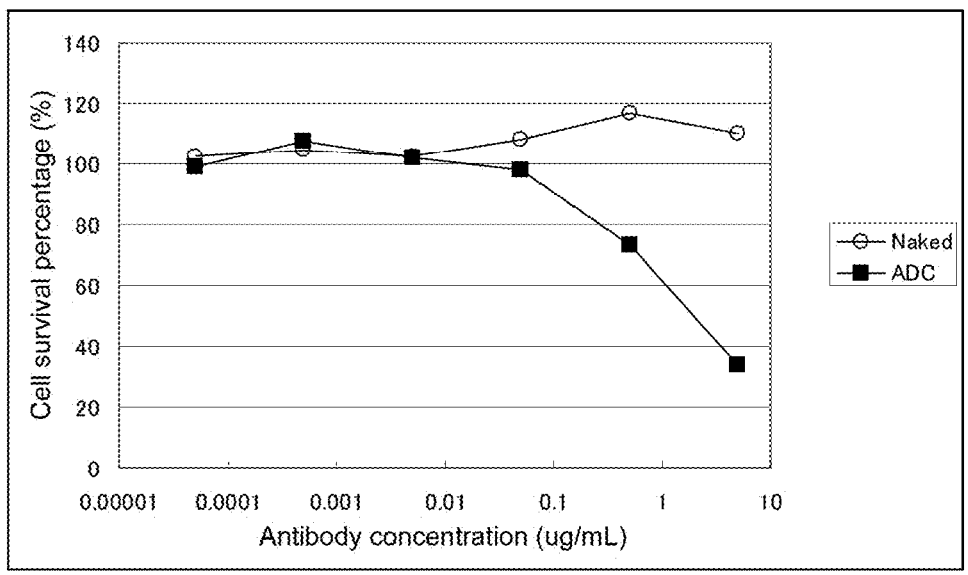
[Figure 8]
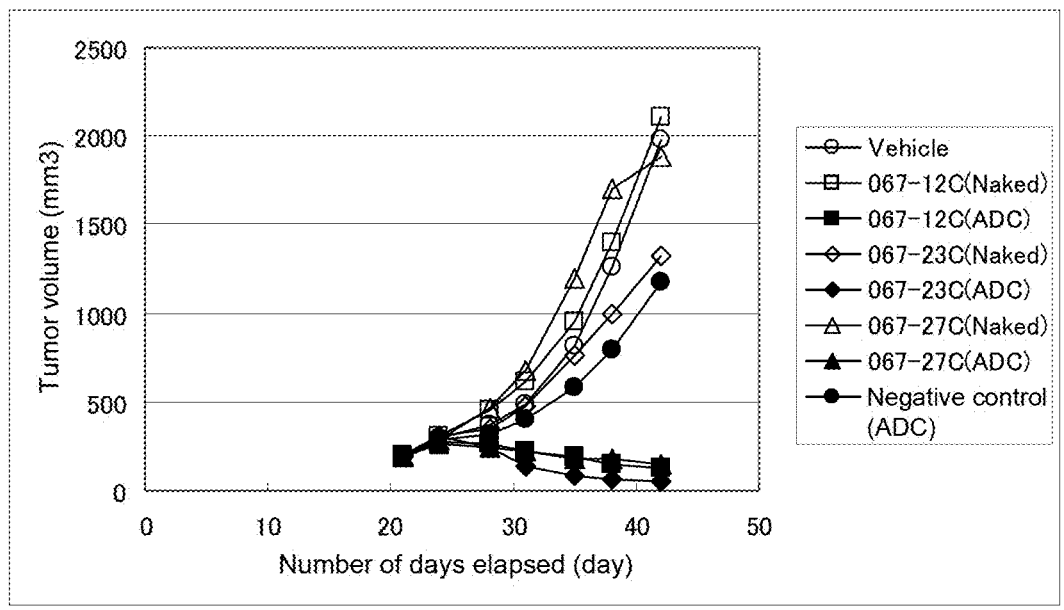

SEQUENCE LISTING

<160> NUMBER OF SEQ ID NOS: 94

<210> SEQ ID NO 1
<211> LENGTH: 2490
<212> TYPE: DNA
<213> ORGANISM: human
<220> FEATURE:
<221> NAME/KEY: CDS
<222> LOCATION: (1)..(2490)

<400> SEQUENCE: 1

```
atg ggg ctc cct cgt gga cct ctc gcg tct ctc ctc ctt ctc cag gtt        48
Met Gly Leu Pro Arg Gly Pro Leu Ala Ser Leu Leu Leu Leu Gln Val
1               5                   10                  15 tgc tgg ctg cag tgc gcg gcc tcc gag ccg tgc cgg gcg gtc ttc agg        96
Cys Trp Leu Gln Cys Ala Ala Ser Glu Pro Cys Arg Ala Val Phe Arg
                20                  25                  30 gag gct gaa gtg acc ttg gag gcg gga ggc gcg gag cag gag ccc ggc       144
Glu Ala Glu Val Thr Leu Glu Ala Gly Gly Ala Glu Gln Glu Pro Gly
            35                  40                  45 cag gcg ctg ggg aaa gta ttc atg ggc tgc cct ggg caa gag cca gct       192
Gln Ala Leu Gly Lys Val Phe Met Gly Cys Pro Gly Gln Glu Pro Ala
        50                  55                  60 ctg ttt agc act gat aat gat gac ttc act gtg cgg aat ggc gag aca       240
Leu Phe Ser Thr Asp Asn Asp Asp Phe Thr Val Arg Asn Gly Glu Thr
65                  70                  75                  80 gtc cag gaa aga agg tca ctg aag gaa agg aat cca ttg aag atc ttc       288
Val Gln Glu Arg Arg Ser Leu Lys Glu Arg Asn Pro Leu Lys Ile Phe
                85                  90                  95 cca tcc aaa cgt atc tta cga aga cac aag aga gat tgg gtg gtt gct       336
Pro Ser Lys Arg Ile Leu Arg Arg His Lys Arg Asp Trp Val Val Ala
                100                 105                 110 cca ata tct gtc cct gaa aat ggc aag ggt ccc ttc ccc cag aga ctg       384
Pro Ile Ser Val Pro Glu Asn Gly Lys Gly Pro Phe Pro Gln Arg Leu
            115                 120                 125 aat cag ctc aag tct aat aaa gat aga gac acc aag att ttc tac agc       432
Asn Gln Leu Lys Ser Asn Lys Asp Arg Asp Thr Lys Ile Phe Tyr Ser
        130                 135                 140 atc acg ggg ccg ggg gca gac agc ccc cct gag ggt gtc ttc gct gta       480
Ile Thr Gly Pro Gly Ala Asp Ser Pro Pro Glu Gly Val Phe Ala Val
145                 150                 155                 160 gag aag gag aca ggc tgg ttg ttg ttg aat aag cca ctg gac cgg gag       528
Glu Lys Glu Thr Gly Trp Leu Leu Leu Asn Lys Pro Leu Asp Arg Glu
                165                 170                 175 gag att gcc aag tat gag ctc ttt ggc cac gct gtg tca gag aat ggt       576
Glu Ile Ala Lys Tyr Glu Leu Phe Gly His Ala Val Ser Glu Asn Gly
                180                 185                 190 gcc tca gtg gag gac ccc atg aac atc tcc atc atc gtg acc gac cag       624
```

```
                Ala Ser Val Glu Asp Pro Met Asn Ile Ser Ile Ile Val Thr Asp Gln
                            195                 200                 205 aat gac cac aag ccc aag ttt acc cag gac acc ttc cga ggg agt gtc          672
Asn Asp His Lys Pro Lys Phe Thr Gln Asp Thr Phe Arg Gly Ser Val
210                 215                 220 tta gag gga gtc cta cca ggt act tct gtg atg cag gtg aca gcc acg          720
Leu Glu Gly Val Leu Pro Gly Thr Ser Val Met Gln Val Thr Ala Thr
225                 230                 235                 240 gat gag gat gat gcc atc tac acc tac aat ggg gtg gtt gct tac tcc          768
Asp Glu Asp Asp Ala Ile Tyr Thr Tyr Asn Gly Val Val Ala Tyr Ser
                    245                 250                 255 atc cat agc caa gaa cca aag gac cca cac gac ctc atg ttc acc att          816
Ile His Ser Gln Glu Pro Lys Asp Pro His Asp Leu Met Phe Thr Ile
                260                 265                 270 cac cgg agc aca ggc acc atc agc gtc atc tcc agt ggc ctg gac cgg          864
His Arg Ser Thr Gly Thr Ile Ser Val Ile Ser Ser Gly Leu Asp Arg
            275                 280                 285 gaa aaa gtc cct gag tac aca ctg acc atc cag gcc aca gac atg gat          912
Glu Lys Val Pro Glu Tyr Thr Leu Thr Ile Gln Ala Thr Asp Met Asp
        290                 295                 300 ggg gac ggc tcc acc acc acg gca gtg gca gta gtg gag atc ctt gat          960
Gly Asp Gly Ser Thr Thr Thr Ala Val Ala Val Val Glu Ile Leu Asp
305                 310                 315                 320 gcc aat gac aat gct ccc atg ttt gac ccc cag aag tac gag gcc cat         1008
Ala Asn Asp Asn Ala Pro Met Phe Asp Pro Gln Lys Tyr Glu Ala His
                    325                 330                 335 gtg cct gag aat gca gtg ggc cat gag gtg cag agg ctg acg gtc act         1056
Val Pro Glu Asn Ala Val Gly His Glu Val Gln Arg Leu Thr Val Thr
                340                 345                 350 gat ctg gac gcc ccc aac tca cca gcg tgg cgt gcc acc tac ctt atc         1104
Asp Leu Asp Ala Pro Asn Ser Pro Ala Trp Arg Ala Thr Tyr Leu Ile
            355                 360                 365 atg ggc ggt gac gac ggg gac cat ttt acc atc acc acc cac cct gag         1152
Met Gly Gly Asp Asp Gly Asp His Phe Thr Ile Thr Thr His Pro Glu
        370                 375                 380 agc aac cag ggc atc ctg aca acc agg aag ggt ttg gat ttt gag gcc         1200
Ser Asn Gln Gly Ile Leu Thr Thr Arg Lys Gly Leu Asp Phe Glu Ala
385                 390                 395                 400 aaa aac cag cac acc ctg tac gtt gaa gtg acc aac gag gcc cct ttt         1248
Lys Asn Gln His Thr Leu Tyr Val Glu Val Thr Asn Glu Ala Pro Phe
                    405                 410                 415 gtg ctg aag ctc cca acc tcc aca gcc acc ata gtg gtc cac gtg gag         1296
Val Leu Lys Leu Pro Thr Ser Thr Ala Thr Ile Val Val His Val Glu
                420                 425                 430 gat gtg aat gag gca cct gtg ttt gtc cca ccc tcc aaa gtc gtt gag         1344
Asp Val Asn Glu Ala Pro Val Phe Val Pro Pro Ser Lys Val Val Glu
            435                 440                 445 gtc cag gag ggc atc ccc act ggg gag cct gtg tgt gtc tac act gca         1392
Val Gln Glu Gly Ile Pro Thr Gly Glu Pro Val Cys Val Tyr Thr Ala
        450                 455                 460 gaa gac cct gac aag gag aat caa aag atc agc tac cgc atc ctg aga         1440
Glu Asp Pro Asp Lys Glu Asn Gln Lys Ile Ser Tyr Arg Ile Leu Arg
465                 470                 475                 480 gac cca gca ggg tgg cta gcc atg gac cca gac agt ggg cag gtc aca         1488
Asp Pro Ala Gly Trp Leu Ala Met Asp Pro Asp Ser Gly Gln Val Thr
                    485                 490                 495 gct gtg ggc acc ctc gac cgt gag gat gag cag ttt gtg agg aac aac         1536
Ala Val Gly Thr Leu Asp Arg Glu Asp Glu Gln Phe Val Arg Asn Asn
                500                 505                 510
```

```
atc tat gaa gtc atg gtc ttg gcc atg gac aat gga agc cct ccc acc         1584
Ile Tyr Glu Val Met Val Leu Ala Met Asp Asn Gly Ser Pro Pro Thr
        515                 520                 525 act ggc acg gga acc ctt ctg cta aca ctg att gat gtc aat gac cat         1632
Thr Gly Thr Gly Thr Leu Leu Leu Thr Leu Ile Asp Val Asn Asp His
530                 535                 540 ggc cca gtc cct gag ccc cgt cag atc acc atc tgc aac caa agc cct         1680
Gly Pro Val Pro Glu Pro Arg Gln Ile Thr Ile Cys Asn Gln Ser Pro
545                 550                 555                 560 gtg cgc cag gtg ctg aac atc acg gac aag gac ctg tct ccc cac acc         1728
Val Arg Gln Val Leu Asn Ile Thr Asp Lys Asp Leu Ser Pro His Thr
                565                 570                 575 tcc cct ttc cag gcc cag ctc aca gat gac tca gac atc tac tgg acg         1776
Ser Pro Phe Gln Ala Gln Leu Thr Asp Asp Ser Asp Ile Tyr Trp Thr
            580                 585                 590 gca gag gtc aac gag gaa ggt gac aca gtg gtc ttg tcc ctg aag aag         1824
Ala Glu Val Asn Glu Glu Gly Asp Thr Val Val Leu Ser Leu Lys Lys
        595                 600                 605 ttc ctg aag cag gat aca tat gac gtg cac ctt tct ctg tct gac cat         1872
Phe Leu Lys Gln Asp Thr Tyr Asp Val His Leu Ser Leu Ser Asp His
610                 615                 620 ggc aac aaa gag cag ctg acg gtg atc agg gcc act gtg tgc gac tgc         1920
Gly Asn Lys Glu Gln Leu Thr Val Ile Arg Ala Thr Val Cys Asp Cys
625                 630                 635                 640 cat ggc cat gtc gaa acc tgc cct gga ccc tgg aag gga ggt ttc atc         1968
His Gly His Val Glu Thr Cys Pro Gly Pro Trp Lys Gly Gly Phe Ile
                645                 650                 655 ctc cct gtg ctg ggg gct gtc ctg gct ctg ctg ttc ctc ctg ctg gtg         2016
Leu Pro Val Leu Gly Ala Val Leu Ala Leu Leu Phe Leu Leu Leu Val
            660                 665                 670 ctg ctt ttg ttg gtg aga aag aag cgg aag atc aag gag ccc ctc cta         2064
Leu Leu Leu Leu Val Arg Lys Lys Arg Lys Ile Lys Glu Pro Leu Leu
        675                 680                 685 ctc cca gaa gat gac acc cgt gac aac gtc ttc tac tat ggc gaa gag         2112
Leu Pro Glu Asp Asp Thr Arg Asp Asn Val Phe Tyr Tyr Gly Glu Glu
690                 695                 700 ggg ggt ggc gaa gag gac cag gac tat gac atc acc cag ctc cac cga         2160
Gly Gly Gly Glu Glu Asp Gln Asp Tyr Asp Ile Thr Gln Leu His Arg
705                 710                 715                 720 ggt ctg gag gcc agg ccg gag gtg gtt ctc cgc aat gac gtg gca cca         2208
Gly Leu Glu Ala Arg Pro Glu Val Val Leu Arg Asn Asp Val Ala Pro
                725                 730                 735 acc atc atc ccg aca ccc atg tac cgt cct cgg cca gcc aac cca gat         2256
Thr Ile Ile Pro Thr Pro Met Tyr Arg Pro Arg Pro Ala Asn Pro Asp
            740                 745                 750 gaa atc ggc aac ttt ata att gag aac ctg aag gcg gct aac aca gac         2304
Glu Ile Gly Asn Phe Ile Ile Glu Asn Leu Lys Ala Ala Asn Thr Asp
        755                 760                 765 ccc aca gcc ccg ccc tac gac acc ctc ttg gtg ttc gac tat gag ggc         2352
Pro Thr Ala Pro Pro Tyr Asp Thr Leu Leu Val Phe Asp Tyr Glu Gly
770                 775                 780 agc ggc tcc gac gcc gcg tcc ctg agc tcc ctc acc tcc tcc gcc tcc         2400
Ser Gly Ser Asp Ala Ala Ser Leu Ser Ser Leu Thr Ser Ser Ala Ser
785                 790                 795                 800 gac caa gac caa gat tac gat tat ctg aac gag tgg ggc agc cgc ttc         2448
Asp Gln Asp Gln Asp Tyr Asp Tyr Leu Asn Glu Trp Gly Ser Arg Phe
                805                 810                 815 aag aag ctg gca gac atg tac ggt ggc ggg gag gac gac tag              2490
Lys Lys Leu Ala Asp Met Tyr Gly Gly Gly Glu Asp Asp
            820                 825
```

```
<210> SEQ ID NO 2
<211> LENGTH: 829
<212> TYPE: PRT
<213> ORGANISM: human

<400> SEQUENCE: 2

Met Gly Leu Pro Arg Gly Pro Leu Ala Ser Leu Leu Leu Leu Gln Val
1               5                   10                  15

Cys Trp Leu Gln Cys Ala Ala Ser Glu Pro Cys Arg Ala Val Phe Arg
            20                  25                  30

Glu Ala Glu Val Thr Leu Glu Ala Gly Gly Ala Glu Gln Glu Pro Gly
        35                  40                  45

Gln Ala Leu Gly Lys Val Phe Met Gly Cys Pro Gly Gln Glu Pro Ala
    50                  55                  60

Leu Phe Ser Thr Asp Asn Asp Phe Thr Val Arg Asn Gly Glu Thr
65                  70                  75                  80

Val Gln Glu Arg Arg Ser Leu Lys Glu Arg Asn Pro Leu Lys Ile Phe
                85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
        115                 120                 125

Asn Gln Leu Lys Ser Asn Lys Asp Arg Asp Thr Lys Ile Phe Tyr Ser
    130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190

Ala Ser Val Glu Asp Pro Met Asn Ile Ser Ile Ile Val Thr Asp Gln
        195                 200                 205

Asn Asp His Lys Pro Lys Phe Thr Gln Asp Thr Phe Arg Gly Ser Val
    210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255

Ile His Ser Gln Glu Pro Lys Asp Pro His Asp Leu Met Phe Thr Ile
            260                 265                 270

His Arg Ser Thr Gly Thr Ile Ser Val Ile Ser Ser Gly Leu Asp Arg
        275                 280                 285

Glu Lys Val Pro Glu Tyr Thr Leu Thr Ile Gln Ala Thr Asp Met Asp
    290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
            340                 345                 350

Asp Leu Asp Ala Pro Asn Ser Pro Ala Trp Arg Ala Thr Tyr Leu Ile
        355                 360                 365

Met Gly Gly Asp Asp Gly Asp His Phe Thr Ile Thr Thr His Pro Glu
```

```
            370                 375                 380
Ser Asn Gln Gly Ile Leu Thr Thr Arg Lys Gly Leu Asp Phe Glu Ala
385                 390                 395                 400
Lys Asn Gln His Thr Leu Tyr Val Glu Val Thr Asn Glu Ala Pro Phe
                405                 410                 415
Val Leu Lys Leu Pro Thr Ser Thr Ala Thr Ile Val Val His Val Glu
            420                 425                 430
Asp Val Asn Glu Ala Pro Val Phe Val Pro Pro Ser Lys Val Val Glu
            435                 440                 445
Val Gln Glu Gly Ile Pro Thr Gly Glu Pro Val Cys Val Tyr Thr Ala
        450                 455                 460
Glu Asp Pro Asp Lys Glu Asn Gln Lys Ile Ser Tyr Arg Ile Leu Arg
465                 470                 475                 480
Asp Pro Ala Gly Trp Leu Ala Met Asp Pro Asp Ser Gly Gln Val Thr
                485                 490                 495
Ala Val Gly Thr Leu Asp Arg Glu Asp Glu Gln Phe Val Arg Asn Asn
            500                 505                 510
Ile Tyr Glu Val Met Val Leu Ala Met Asp Asn Gly Ser Pro Pro Thr
            515                 520                 525
Thr Gly Thr Gly Thr Leu Leu Leu Thr Leu Ile Asp Val Asn Asp His
        530                 535                 540
Gly Pro Val Pro Glu Pro Arg Gln Ile Thr Ile Cys Asn Gln Ser Pro
545                 550                 555                 560
Val Arg Gln Val Leu Asn Ile Thr Asp Lys Asp Leu Ser Pro His Thr
                565                 570                 575
Ser Pro Phe Gln Ala Gln Leu Thr Asp Asp Ser Asp Ile Tyr Trp Thr
            580                 585                 590
Ala Glu Val Asn Glu Gly Asp Thr Val Val Leu Ser Leu Lys Lys
            595                 600                 605
Phe Leu Lys Gln Asp Thr Tyr Asp Val His Leu Ser Leu Ser Asp His
        610                 615                 620
Gly Asn Lys Glu Gln Leu Thr Val Ile Arg Ala Thr Val Cys Asp Cys
625                 630                 635                 640
His Gly His Val Glu Thr Cys Pro Gly Pro Trp Lys Gly Gly Phe Ile
                645                 650                 655
Leu Pro Val Leu Gly Ala Val Leu Ala Leu Leu Phe Leu Leu Leu Val
            660                 665                 670
Leu Leu Leu Leu Val Arg Lys Lys Arg Lys Ile Lys Glu Pro Leu Leu
            675                 680                 685
Leu Pro Glu Asp Asp Thr Arg Asp Asn Val Phe Tyr Tyr Gly Glu Glu
        690                 695                 700
Gly Gly Gly Glu Glu Asp Gln Asp Tyr Asp Ile Thr Gln Leu His Arg
705                 710                 715                 720
Gly Leu Glu Ala Arg Pro Glu Val Val Leu Arg Asn Asp Val Ala Pro
                725                 730                 735
Thr Ile Ile Pro Thr Pro Met Tyr Arg Pro Arg Pro Ala Asn Pro Asp
            740                 745                 750
Glu Ile Gly Asn Phe Ile Ile Glu Asn Leu Lys Ala Ala Asn Thr Asp
            755                 760                 765
Pro Thr Ala Pro Pro Tyr Asp Thr Leu Leu Val Phe Asp Tyr Glu Gly
        770                 775                 780
Ser Gly Ser Asp Ala Ala Ser Leu Ser Ser Leu Thr Ser Ser Ala Ser
785                 790                 795                 800
```

Asp Gln Asp Gln Asp Tyr Asp Tyr Leu Asn Glu Trp Gly Ser Arg Phe
            805                 810                 815

Lys Lys Leu Ala Asp Met Tyr Gly Gly Gly Glu Asp Asp
            820                 825

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
cgcggtacca tggggctccc tcgt                                            24

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
ccgtctagat aacctccctt ccagggtcc                                       29

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
gayatccagc tgactcagcc                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
gayattgttc tcwcccagtc                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
gayattgtgm tmactcagtc                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic

DNA

<400> SEQUENCE: 8
gayattgtgy tracacagtc                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
gayattgtra tgacmcagtc                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
gayattmaga tramccagtc                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
gayattcaga tgaydcagtc                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
gayatycaga tgacacagac                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
gayattgttc tcawccagtc                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
gayattgwgc tsacccaatc                                                     20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
gayattstra tgacccartc                                                     20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
gayrttktga tgacccarac                                                     20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
gayattgtga tgacbcagkc                                                     20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
gayattgtga taacycagga                                                     20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
gayattgtga tgacccagwt                                                     20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
gayattgtga tgacacaacc                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
gayattttgc tgactcagtc                                              20

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
ggsaccaarc tggaaatmaa a                                            21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
gggacaaagt tggaaataaa a                                            21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
gggaccaagc tggagctgaa a                                            21

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
atgragwcac akwcycaggt cttt                                         24

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26

```
atggagacag acacactcct gctat                                            25
```

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27

```
atggagwcag acacactsct gytatgggt                                        29
```

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: misc_feature
<222> LOCATION: (27)..(27)
<223> OTHER INFORMATION: n is inosine

<400> SEQUENCE: 28

```
atgaggrccc ctgctcagwt tyttggnwtc tt                                    32
```

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29

```
atgggcwtca agatgragtc acakwyycwg g                                     31
```

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30

```
atgagtgtgc ycactcaggt cctggsgtt                                        29
```

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31

```
atgtggggay cgktttyamm cttttcaatt g                                     31
```

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic

```
                    DNA

<400> SEQUENCE: 32
atggaagccc cagctcagct tctcttcc                                    28

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: misc_feature
<222> LOCATION: (1)..(26)
<223> OTHER INFORMATION: any n is inosine

<400> SEQUENCE: 33
atgagnmmkt cnmttcantt cytggg                                      26

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: misc_feature
<222> LOCATION: (1)..(26)
<223> OTHER INFORMATION: any n is inosine

<400> SEQUENCE: 34
atgakgthcy cngctcagyt yctnrg                                      26

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
atggtrtccw casctcagtt ccttg                                       25

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
atgtatatat gtttgttgtc tatttct                                     27

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
atgaagttgc ctgttaggct gttggtgct                                   29
```

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
atggatttwc argtgcagat twtcagctt                                       29

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
atggtyctya tvtccttgct gttctgg                                         27

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
atggtyctya tvttrctgct gctatgg                                         27

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
actggatggt gggaagatgg a                                               21

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
atggratgsa gctgkgtmat sctctt                                          26

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
atgracttcg ggytgagctk ggtttt                                          26

```
<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
atggctgtct tggggctgct cttct                                       25

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
atggrcagrc ttacwtyy                                               18

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
saggtsmarc tksagsagtc wgg                                         23

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 47 cascccatc dgtctatcc                                               19

<210> SEQ ID NO 48
<211> LENGTH: 5
<212> TYPE: PRT
<213> ORGANISM: mouse

<400> SEQUENCE: 48

Asp Tyr Asn Ile Asp
1               5

<210> SEQ ID NO 49
<211> LENGTH: 5
<212> TYPE: PRT
<213> ORGANISM: mouse

<400> SEQUENCE: 49

Ser Tyr Gly Val His
1               5

<210> SEQ ID NO 50
<211> LENGTH: 5
<212> TYPE: PRT
<213> ORGANISM: mouse
```

```
<400> SEQUENCE: 50

Gly Tyr Tyr Met His
1               5

<210> SEQ ID NO 51
<211> LENGTH: 5
<212> TYPE: PRT
<213> ORGANISM: mouse

<400> SEQUENCE: 51

Ala Tyr Asn Met His
1               5

<210> SEQ ID NO 52
<211> LENGTH: 5
<212> TYPE: PRT
<213> ORGANISM: mouse

<400> SEQUENCE: 52

Asp Tyr Asn Met Asp
1               5

<210> SEQ ID NO 53
<211> LENGTH: 5
<212> TYPE: PRT
<213> ORGANISM: mouse

<400> SEQUENCE: 53

Asp His Asn Ile Asp
1               5

<210> SEQ ID NO 54
<211> LENGTH: 5
<212> TYPE: PRT
<213> ORGANISM: mouse

<400> SEQUENCE: 54

Thr Tyr Trp Ile Tyr
1               5

<210> SEQ ID NO 55
<211> LENGTH: 5
<212> TYPE: PRT
<213> ORGANISM: mouse

<400> SEQUENCE: 55

Ser Tyr Trp Met Asn
1               5

<210> SEQ ID NO 56
<211> LENGTH: 17
<212> TYPE: PRT
<213> ORGANISM: mouse

<400> SEQUENCE: 56

Tyr Ile Phe Pro Asn Asn Gly Gly Phe Gly Tyr Asn Gln Lys Phe Lys
1               5                   10                  15

Asn

<210> SEQ ID NO 57
<211> LENGTH: 17
<212> TYPE: PRT
<213> ORGANISM: mouse
```

-continued

```
<400> SEQUENCE: 57

Phe Ile Asp Pro Tyr Ser Gly Ile Ile Thr Tyr Asn Gln Thr Phe Lys
1               5                   10                  15
Gly

<210> SEQ ID NO 58
<211> LENGTH: 16
<212> TYPE: PRT
<213> ORGANISM: mouse

<400> SEQUENCE: 58

Val Ile Trp Ala Gly Gly Asn Thr Ile Tyr Asn Ser Ala Leu Met Ser
1               5                   10                  15

<210> SEQ ID NO 59
<211> LENGTH: 17
<212> TYPE: PRT
<213> ORGANISM: mouse

<400> SEQUENCE: 59

Glu Ile Asn Pro Ser Thr Gly Gly Thr Thr Tyr Asn Gln Lys Phe Lys
1               5                   10                  15
Ala

<210> SEQ ID NO 60
<211> LENGTH: 17
<212> TYPE: PRT
<213> ORGANISM: mouse

<400> SEQUENCE: 60

Tyr Ile Phe Pro Asn Asn Gly Gly Ala Gly Tyr Asn Pro Lys Phe Lys
1               5                   10                  15
Asn

<210> SEQ ID NO 61
<211> LENGTH: 17
<212> TYPE: PRT
<213> ORGANISM: mouse

<400> SEQUENCE: 61

Tyr Ile Tyr Pro Ser Asn Gly Gly Thr Gly Tyr Asn Gln Lys Phe Lys
1               5                   10                  15
Asn

<210> SEQ ID NO 62
<211> LENGTH: 17
<212> TYPE: PRT
<213> ORGANISM: mouse

<400> SEQUENCE: 62

Glu Ile Asp Pro Ser Asp Asn Tyr Thr Tyr Tyr Ser Gln Lys Phe Lys
1               5                   10                  15
Gly

<210> SEQ ID NO 63
<211> LENGTH: 17
<212> TYPE: PRT
<213> ORGANISM: mouse

<400> SEQUENCE: 63

Arg Ile His Pro Ser Asp Ser Glu Thr His Tyr Asn Gln Lys Phe Lys
```

```
1               5                   10                  15
Ser

<210> SEQ ID NO 64
<211> LENGTH: 16
<212> TYPE: PRT
<213> ORGANISM: mouse

<400> SEQUENCE: 64

Val Ile Trp Ser Gly Gly Ser Thr Asp Tyr Asn Ala Ala Phe Ile Ser
1               5                   10                  15

<210> SEQ ID NO 65
<211> LENGTH: 13
<212> TYPE: PRT
<213> ORGANISM: mouse

<400> SEQUENCE: 65

Pro Tyr Gly Asn Tyr Asp Tyr Tyr Tyr Ala Met Asp Tyr
1               5                   10

<210> SEQ ID NO 66
<211> LENGTH: 8
<212> TYPE: PRT
<213> ORGANISM: mouse

<400> SEQUENCE: 66

Asn Ser Asn Asn Gly Phe Ala Tyr
1               5

<210> SEQ ID NO 67
<211> LENGTH: 10
<212> TYPE: PRT
<213> ORGANISM: mouse

<400> SEQUENCE: 67

Arg Gly Tyr Tyr Asp Gly Gly Phe Asp Tyr
1               5                   10

<210> SEQ ID NO 68
<211> LENGTH: 14
<212> TYPE: PRT
<213> ORGANISM: mouse

<400> SEQUENCE: 68

Pro His Tyr Gly Asp Tyr Ala Gly Phe Tyr Ala Leu Asp His
1               5                   10

<210> SEQ ID NO 69
<211> LENGTH: 9
<212> TYPE: PRT
<213> ORGANISM: mouse

<400> SEQUENCE: 69

Asp Ser Asn Tyr Val Gly Phe Ala Phe
1               5

<210> SEQ ID NO 70
<211> LENGTH: 16
<212> TYPE: PRT
<213> ORGANISM: mouse

<400> SEQUENCE: 70

Lys Met Glu Ala Tyr Tyr Ser Tyr Asp Tyr Tyr Tyr Ala Met Asp Tyr
```

```
<210> SEQ ID NO 71
<211> LENGTH: 13
<212> TYPE: PRT
<213> ORGANISM: mouse

<400> SEQUENCE: 71

Pro Tyr Gly Asn Asp Asp Tyr Tyr Ala Met Asp Tyr
1               5                   10

<210> SEQ ID NO 72
<211> LENGTH: 8
<212> TYPE: PRT
<213> ORGANISM: mouse

<400> SEQUENCE: 72

Arg His Trp Asp Gly Phe Ala Tyr
1               5

<210> SEQ ID NO 73
<211> LENGTH: 8
<212> TYPE: PRT
<213> ORGANISM: mouse

<400> SEQUENCE: 73

Trp Asp Tyr Asp His Phe Asp Tyr
1               5

<210> SEQ ID NO 74
<211> LENGTH: 12
<212> TYPE: PRT
<213> ORGANISM: mouse

<400> SEQUENCE: 74

Ser Ala Ser Ser Ser Val Ser Ser Gly Asn Phe His
1               5                   10

<210> SEQ ID NO 75
<211> LENGTH: 11
<212> TYPE: PRT
<213> ORGANISM: mouse

<400> SEQUENCE: 75

Arg Ala Ser Lys Ser Ile Ser Lys Tyr Leu Ala
1               5                   10

<210> SEQ ID NO 76
<211> LENGTH: 11
<212> TYPE: PRT
<213> ORGANISM: mouse

<400> SEQUENCE: 76

Arg Thr Ser Glu Asn Ile Tyr Ser Asn Leu Ala
1               5                   10

<210> SEQ ID NO 77
<211> LENGTH: 11
<212> TYPE: PRT
<213> ORGANISM: mouse

<400> SEQUENCE: 77

Arg Ala Ser Gln Asp Ile Ser Asn Tyr Leu Asn
1               5                   10
```

```
<210> SEQ ID NO 78
<211> LENGTH: 11
<212> TYPE: PRT
<213> ORGANISM: mouse

<400> SEQUENCE: 78

Arg Ala Ser Gln Asp Ile Thr Asn Tyr Leu Asn
1               5                   10

<210> SEQ ID NO 79
<211> LENGTH: 11
<212> TYPE: PRT
<213> ORGANISM: mouse

<400> SEQUENCE: 79

Arg Ala Ser Lys Arg Ile Ser Lys Tyr Leu Ala
1               5                   10

<210> SEQ ID NO 80
<211> LENGTH: 12
<212> TYPE: PRT
<213> ORGANISM: mouse

<400> SEQUENCE: 80

Ser Ala Ser Ser Ser Val Ser Ser Arg Tyr Leu His
1               5                   10

<210> SEQ ID NO 81
<211> LENGTH: 7
<212> TYPE: PRT
<213> ORGANISM: mouse

<400> SEQUENCE: 81

Arg Thr Ser Asn Leu Ala Ser
1               5

<210> SEQ ID NO 82
<211> LENGTH: 7
<212> TYPE: PRT
<213> ORGANISM: mouse

<400> SEQUENCE: 82

Ser Gly Ser Thr Leu Gln Ser
1               5

<210> SEQ ID NO 83
<211> LENGTH: 7
<212> TYPE: PRT
<213> ORGANISM: mouse

<400> SEQUENCE: 83

Tyr Thr Ser Arg Leu His Ser
1               5

<210> SEQ ID NO 84
<211> LENGTH: 7
<212> TYPE: PRT
<213> ORGANISM: mouse

<400> SEQUENCE: 84

Ala Ala Lys Asn Leu Ala Asp
1               5

<210> SEQ ID NO 85
```

```
<211> LENGTH: 7
<212> TYPE: PRT
<213> ORGANISM: mouse

<400> SEQUENCE: 85

Gly Thr Ser Asn Leu Ala Ser
1               5

<210> SEQ ID NO 86
<211> LENGTH: 9
<212> TYPE: PRT
<213> ORGANISM: mouse

<400> SEQUENCE: 86

Gln Gln His Tyr Glu Tyr Pro Tyr Thr
1               5

<210> SEQ ID NO 87
<211> LENGTH: 9
<212> TYPE: PRT
<213> ORGANISM: mouse

<400> SEQUENCE: 87

Gln Gln Tyr Ser Lys Phe Pro Arg Thr
1               5

<210> SEQ ID NO 88
<211> LENGTH: 9
<212> TYPE: PRT
<213> ORGANISM: mouse

<400> SEQUENCE: 88

Gln Gln Asp Ser Lys His Pro Arg Thr
1               5

<210> SEQ ID NO 89
<211> LENGTH: 9
<212> TYPE: PRT
<213> ORGANISM: mouse

<400> SEQUENCE: 89

Gln His Phe Tyr Asp Thr Pro Trp Thr
1               5

<210> SEQ ID NO 90
<211> LENGTH: 9
<212> TYPE: PRT
<213> ORGANISM: mouse

<400> SEQUENCE: 90

Gln Gln His Asn Glu Tyr Pro Trp Thr
1               5

<210> SEQ ID NO 91
<211> LENGTH: 9
<212> TYPE: PRT
<213> ORGANISM: mouse

<400> SEQUENCE: 91

Gln Gln Tyr Asn Glu Tyr Pro Tyr Thr
1               5

<210> SEQ ID NO 92
<211> LENGTH: 9
<212> TYPE: PRT
```

```
<213> ORGANISM: mouse

<400> SEQUENCE: 92

Gln Gln Tyr Tyr Glu Tyr Pro Tyr Thr
1               5

<210> SEQ ID NO 93
<211> LENGTH: 9
<212> TYPE: PRT
<213> ORGANISM: mouse

<400> SEQUENCE: 93

Gln Gln Trp Ser Gly Tyr Pro Pro Thr
1               5

<210> SEQ ID NO 94
<211> LENGTH: 9
<212> TYPE: PRT
<213> ORGANISM: mouse

<400> SEQUENCE: 94

Gln Pro Tyr His Ser Asp Pro Phe Thr
1               5
```

DRUG CONJUGATE COMPRISING ANTI-CDH3 (P-CADHERIN) ANTIBODY

REFERENCE TO SEQUENCE LISTING SUBMITTED VIA EFS-WEB

This application includes an electronically submitted sequence listing in .txt format. The .txt file contains a sequence listing entitled "2015-10-13_2870-0590PUS1_ST25.txt" created on Oct. 13, 2015 and is 37,076 bytes in size. The sequence listing contained in this .txt file is part of the specification and is hereby incorporated by reference herein in its entirety.

TECHNICAL FIELD

The present invention relates to a drug conjugate comprising an anti-CDH3 antibody. The present invention also relates to a method of using the drug conjugate comprising an anti-CDH3 antibody.

BACKGROUND ART

Cancer is a serious disease that accounts for a major cause of death. However, therapeutic needs therefor have not yet been met. In recent years, in order to overcome the problem of conventional chemotherapy that causes damage even to normal cells, studies have been intensively conducted regarding cancer therapy using molecularly targeted drugs, in which a drug targeting a specific molecule that is expressed specifically in a cancer cell is designed, and the therapy is then carried out using the drug.

CDH3 is a cell surface antigen that has been identified as a target thereof CDH3 is a membrane protein that has been discovered as a molecule that is calcium-dependently associated with hemophilic cell adhesion (Yoshida and Takeichi, Cell 28: 217-224, 1982). A protein, which has cadherin repeats consisting of approximately 110 amino acid residues having high homology to one another, is referred to as a "cadherin superfamily," and CDH3 is a main member of the cadherin superfamily.

An increase in the expression of CDH3 in certain types of cancer cells has been reported. Thus, cancer therapy, in which an antibody against cancer cells with higher expression of CDH3 in cancer tissues than in normal tissues is used, has been studied (WO2002/097395 and WO2007/102525).

A large number of antibody drugs have already been placed on the market as molecular-targeted drugs, and a majority of the drugs have antibody-dependent cellular cytotoxicity (ADCC) as a principal mode of action. However, their drug effects are not necessarily sufficient, and thus, technology development is proceeding towards the achievement of a stronger antitumor effect.

An effective means for enhancing the antitumor ability of an antibody is the binding of the antibody to a drug having strong toxicity (toxin). If toxin alone were administered to a patient, it would also affect normal tissues, and thereby, it could not be an effective therapeutic means. However, as a result of the binding of the toxin to an antibody that binds to a tumor cell-specific antigen, the toxin is able to achieve a capacity of killing only tumor cells, while it does not affect normal tissues. Such a drug is referred to as an antibody drug conjugate (ADC). That is to say, a toxin shows no toxicity in a state in which it binds to an antibody. However, when a certain type of antibody binds to a target antigen, it is incorporated into the cell thereof and is then decomposed by a lysosome. Accordingly, the certain type of antibody, to which a toxin binds, is incorporated into the cell, and it is then decomposed therein, so that the toxin is released. As a result, the toxin is expressed only in a specific cell, and the cell is then killed by the effect thereof.

Examples of a drug ingredient used in ADC include bacterial protein toxins such as diphtheria toxin, vegetable protein toxins such as ricin, and low-molecular-weight toxins such as auristatin, maytansinoid or calichemicin and the derivatives thereof.

In ADC, a drug that binds to an antibody circulates in the blood and then accumulates in a target tumor, and thereafter, it exhibits its drug effects. The release of a drug in sites other than tumor sites (the release from the antibody) is not necessarily preferable because it is likely to cause side effects. That is, a drug that binds to an antibody is preferably designed such that it is removed from the antibody after it has been incorporated into a cell. In recent years, from the aforementioned viewpoint, a drug (T-DM1) in which a toxin binds to trastuzumab via a non-cleavable linker (SMCC) has been developed by Genentech. Clinical tests have been carried out on the developed drug, and extremely high clinical effects have been obtained. In addition, an antibody drug conjugate, in which an antibody is bound to a drug ingredient via a cleavable linker, has been developed. For example, the development of an antibody drug conjugate, in which a drug is bound to a HuN901 antibody via a disulfide linker (SPP), that targets cancer expressing NCAM antigen, has been promoted by ImmunoGen.

As described above, the concept of cancer therapy using ADC is known. In the present technical field, there is a demand for other drugs for therapy of various cancers such as lung cancer and colon cancer. An example of a drug that is particularly useful for this purpose is a drug conjugate comprising an anti-CDH3 antibody, which has significantly low toxicity but has advantageous therapeutic effectiveness. These and other restrictions and previous problems can be solved by the present invention.

PRIOR ART DOCUMENTS

Patent Document

Patent Document 1: WO2002/097395
Patent Document 2: WO2007/102525

Non Patent Document

Non Patent Document 1: Yoshida and Takeichi, Cell 28: 217-224, 1982

SUMMARY OF INVENTION

Object to be Solved by the Invention

It is an object to be solved by the present invention to provide a drug conjugate comprising an anti-CDH3 antibody that efficiently kills cancer cells expressing CDH3.

Means for Solving the Object

As a result of intensive studies directed towards achieving the aforementioned object, the present inventors have found that an immune complex formed by binding an antibody against CDH3 to a chemotherapeutic agent shows strong cellular cytotoxicity against a cancer cell line that expresses CDH3, thereby completing the present invention.

Specifically, according to the present invention, there is provided an immune complex formed by binding an antibody against CDH3 or a fragment thereof having CDH3 binding ability to a chemotherapeutic agent.

Preferably, in the immune complex of the present invention, the antibody against CDH3 or the fragment thereof having CDH3 binding ability shows cytotoxicity against CDH3-expressing cells.

Preferably, the antibody against CDH3 is produced by antibody-producing cells that are obtained from immunocytes, to which CDH3 or a CDH3-expressing cell has been administered as an immunogen.

Preferably, the antibody is a monoclonal antibody.

Preferably, the antibody is chimerized.

Preferably, the antibody is humanized.

Preferably, the antibody is a human antibody.

Preferably, the antibody comprises the amino acid sequences shown in SEQ ID NOs 48, 56 and 65 as CDR-H1, CDR-H2 and CDR-H3, respectively, and comprises the amino acid sequences shown in SEQ ID NOs. 75, 82 and 86 as CDR-L1, CDR-L2 and CDR-L3, respectively.

Preferably, the antibody comprises the amino acid sequences shown in SEQ ID NOs. 52, 60 and 70 as CDR-H1, CDR-H2 and CDR-H3, respectively, and comprises the amino acid sequences shown in SEQ ID NOs. 75, 82 and 91 as CDR-L1, CDR-L2 and CDR-L3, respectively.

Preferably, the antibody comprises the amino acid sequences shown in SEQ ID NOs. 54, 62 and 72 as CDR-H1, CDR-H2 and CDR-H3, respectively, and comprises the amino acid sequences shown in SEQ ID NOs. 74, 81 and 93 as CDR-L1, CDR-L2 and CDR-L3, respectively.

Preferably, the antibody comprises the amino acid sequences shown in SEQ ID NOs. 55, 63 and 73 as CDR-H1, CDR-H2 and CDR-H3, respectively, and comprises the amino acid sequences shown in SEQ ID NOs. 80, 85 and 94 as CDR-L1, CDR-L2 and CDR-L3, respectively.

Preferably, the antibody comprises the amino acid sequences shown in SEQ ID NOs. 49, 64 and 66 as CDR-H1, CDR-H2 and CDR-H3, respectively, and comprises the amino acid sequences shown in SEQ ID NOs. 76, 84 and 89 as CDR-L1, CDR-L2 and CDR-L3, respectively.

Preferably, the antibody comprises the amino acid sequences shown in SEQ ID NOs. 49, 58 and 68 as CDR-H1, CDR-H2 and CDR-H3, respectively, and comprises the amino acid sequences shown in SEQ ID NOs. 79, 82 and 90 as CDR-L1, CDR-L2 and CDR-L3, respectively.

Preferably, the antibody comprises the amino acid sequences shown in SEQ ID NOs. 53, 61 and 71 as CDR-H1, CDR-H2 and CDR-H3, respectively, and comprises the amino acid sequences shown in SEQ ID NOs. 75, 82 and 92 as CDR-L1, CDR-L2 and CDR-L3, respectively.

Preferably, the antibody comprises the amino acid sequences shown in SEQ ID NOs. 51, 57 and 67 as CDR-H1, CDR-H2 and CDR-H3, respectively, and comprises the amino acid sequences shown in SEQ ID NOs. 78, 83 and 88 as CDR-L1, CDR-L2 and CDR-L3, respectively.

Preferably, the antibody comprises the amino acid sequences shown in SEQ ID NOs. 50, 59 and 69 as CDR-H1, CDR-H2 and CDR-H3, respectively, and comprises the amino acid sequences shown in SEQ ID NOs. 77, 83 and 87 as CDR-L1, CDR-L2 and CDR-L3, respectively.

Preferably, the antibody has amino acid sequences of CDR-H1, CDR-H2 and CDR-H3 consisting of an amino acid sequence having sequence identity of at least 90% with the above described amino acid sequences of the amino acid sequences of CDR-H1, CDR-H2 and CDR-H3 of the aforementioned antibody of the present invention.

Preferably, the CDH3 is the CDH3 of a mammal.

Preferably, the CDH3 is selected from the CDH3s of primates.

Preferably, the CDH3 is selected from the CDH3s of human.

Preferably, the CDH3 is expressed on the surface of a cell.

Preferably, the antibody fragment having CDH3 binding ability is Fab, F(ab')$_2$, or scFv.

Preferably, the chemotherapeutic agent is a cytotoxic substance.

Preferably, the cytotoxic substance is selected from maytansinoid and a derivative thereof Preferably, the cytotoxic substance is selected from auristatin and a derivative thereof Preferably, the maytansinoid and the derivative thereof are selected from DM1, DM3, and DM4.

Preferably, the auristatin and the derivative thereof are selected from MMAE and MMAF.

Preferably, the cytotoxic agent is DM1.

Preferably, 1 to 10 DM1s are bound to a single molecule of the antibody against CDH3 or the fragment thereof having CDH3 binding ability.

Preferably, 3 to 8 DM1s are bound to a single molecule of the antibody against CDH3 or the fragment thereof having CDH3 binding ability.

Preferably, the antibody against CDH3 or the fragment thereof having CDH3 binding ability is bound to the chemotherapeutic agent via a linker.

Preferably, the antibody against CDH3 or the fragment thereof having CDH3 binding ability is bound to the chemotherapeutic agent via an intramolecular disulfide bond in the Fc region of the antibody.

Preferably, the antibody against CDH3 or the fragment thereof having CDH3 binding ability is bound to the chemotherapeutic agent as a result of genetic engineering modification of the Fc region of the antibody.

Preferably, the linker used to bind the antibody against CDH3 or the fragment thereof having CDH3 binding ability to the chemotherapeutic agent is a divalent reactive cross-linking reagent.

Preferably, the linker is selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimide butyric acid N-succinimidyl ester (GMBS), ε-maleimidocaproic acid N-hydroxysuccinimide ester (EMCS), m-maleimide benzoyl-N-hydroxysuccinimide ester (MBS), N-(α-maleimidoacetoxy)-succinimide ester (AMAS), succinimidyl-6-(β-maleimidopropionamide) hexanoate (SMPH), N-succinimidyl 4-(p-maleimidophenyl) butyrate (SMPB), N-(p-maleimidophenyl)isocyanate (PMPI), 6-maleimidocaproyl (MC), maleimidopropanoyl (MP), p-aminobenzyloxycarbonyl (PAB), N-succinimidyl 4(2-pyridylthio)pentanoate (SPP). N-succinimidyl (4-iodoacetyl)aminobenzoate (STAB), and N-succinimidyl (4-(2-pyridylthio)butanoate (SPDB).

Preferably, the linker is cleaved by protease.

Preferably, the linker comprises val-cit.

Preferably, the linker comprises PABA.

Moreover, according to the present invention, there is provided a pharmaceutical composition for treating cancer characterized by overexpression of CDH3, which comprises the immune complex of the present invention.

Preferably, the pharmaceutical composition of the present invention has anticancer action.

Preferably, the cancer is selected from among colorectal cancer, non-small-cell lung cancer, breast cancer, cancer of the head and neck, ovarian cancer, lung cancer, invasive bladder cancer, pancreatic cancer, metastatic brain tumor, thyroid cancer, squamous cell carcinoma of the head and neck, squamous cell carcinoma of the esophagus, squamous cell carcinoma of the lung, squamous cell carcinoma of the skin, melanoma, mammary cancer, pulmonary adenocarcinoma, squamous cell carcinoma of the uterine cervix, squamous cell carcinoma of the pancreas, squamous cell carcinoma of the colon, squamous cell carcinoma of the stomach, prostatic cancer, osteosarcoma, and soft tissue sarcoma.

Advantageous Effects of Invention

The immune complex formed by binding an anti-CDH3 antibody to a chemotherapeutic agent, which is provided by the present invention, shows stronger cellular cytotoxicity against cancer cell lines that express CDH3, than an antibody to which a chemotherapeutic agent is not bound. Therefore, it is anticipated that when the immune complex of the present invention is administered to a patient having cancer cells that express CDH3, it will exhibit high anticancer action thereon. That is to say, the immune complex of the present invention is useful as an anticancer agent.

BRIEF DESCRIPTION OF DRAWINGS

FIG. 1 shows the results of flow cytometry, in which a cell line with forcible expression of human CDH3 was reacted with a commercially available anti-human CDH3 antibody. A: CHO cells, and B: CHO cells with forcible expression of CDH3. a: 0.01 mg/mL anti-CDH3 antibody, b: 0.1 mg/mL anti-CDH3 antibody, and c: 1 mg/mL anti-CDH3 antibody.

FIG. 2 shows the results of typical flow cytometry between the obtained 3 types of antibodies and individual cell lines. A: CHO cells with forcible expression of CDH3, B: CHO cells, and C: lung cancer-derived cell line NCI-H358. a: 0.01 mg/mL anti-CDH3 antibody, b: 0.1 mg/mL anti-CDH3 antibody, and c: 1 mg/mL anti-CDH3 antibody.

FIG. 3 shows the results regarding the expression of CDH3 mRNA in various types of tumor tissues. A: normal tissues, B: various types of cancer tissues, and C the degree of differentiation of pancreatic cancer.

FIG. 4 shows the results regarding the expression of CDH3 in various types of human tumor tissues.

FIG. 5 shows the results of flow cytometry in which individual CDH3 chimeric antibodies were each reacted with the cells mentioned below. A: CHO cells, B: CHO cells with forcible expression of CDH3, and C: lung cancer-derived cell line NCI-H358.

FIG. 6 shows the structure of DM1 SMe.

FIG. 7 shows the results of a cytotoxicity test performed on a CDH3 antibody drug conjugate. ADC: CDH3 antibody drug conjugate, and Naked: drug-unbound CDH3 antibody.

FIG. 8 shows the results of an animal test using a CDH3 antibody drug conjugate. ADC: CDH3 antibody drug conjugate, and Naked: drug-unbound CDH3 antibody.

DESCRIPTION OF EMBODIMENTS OF THE INVENTION

Hereinafter, the present invention will be described more in detail.

The immune complex of the present invention is provided as a drug conjugate comprising an anti-CDH3 antibody that efficiently kills cancer cells.

As an antigen used to produce the antibody of the present invention, CDH3 or a partial peptide thereof can be used. As an example, a soluble CDH3 protein or the like can be used, but the examples of the antigen are not limited thereto.

The antibody used in the present invention may be either a polyclonal antibody or a monoclonal antibody. The antibody of the present invention can be produced by any one of various methods. The method for producing the antibody is well known in the present technical field [see, for example, Sambrook, J et al., Molecular Cloning, Cold Spring Harbor Laboratory Press (1989)].

(a) Production of Polyclonal Antibody

To produce a polyclonal antibody, CDH3 or a partial peptide thereof is administered as an antigen to a mammal such as a rat, a mouse or a rabbit. The amount of an antigen per animal is 0.1 to 100 mg if an adjuvant is not used, and is 1 to 100 µg when an adjuvant is used. Examples of an adjuvant used herein include a Freund's complete adjuvant (FCA), a Freund's incomplete adjuvant (FIA), and an aluminum hydroxide adjuvant. Immunization is mainly carried out by injecting the antigen into the vein, subcutis, abdominal cavity, etc. In addition, immunization intervals are not particularly limited, and the immunization is carried out 1 to 10 times, and more preferably 2 to 5 times, at intervals of several days to several weeks, and preferably at intervals of 2 to 5 weeks. Thereafter, six to sixty days after the final immunization, an antibody titer is measured by enzyme-linked immunosorbent assay (ELISA), enzyme immunoassay (ETA), radio immunoassay (RIA), etc. On the day on which the animal exhibits the greatest antibody titer, blood is collected, and antiserum is then obtained. When purification of an antibody from the antiserum is needed, the antibody can be purified by selecting an appropriate method from known methods such as an ammonium sulfate fractionation method, ion exchange chromatography, gel filtration and affinity chromatography, or by a combined use of these methods.

(b) Production of Monoclonal Antibody

To produce a monoclonal antibody, first of all, CDH3 or a partial peptide thereof is administered as an antigen to a mammal such as a rat, a mouse or a rabbit. The amount of an antigen per animal is 0.1 to 100 mg if an adjuvant is not used, and is 1 to 100 µg when an adjuvant is used. Examples of such an adjuvant used herein include a Freund's complete adjuvant (FCA), a Freund's incomplete adjuvant (FIA), and an aluminum hydroxide adjuvant. Immunization is mainly carried out by injecting the antigen into the vein, subcutis or abdominal cavity. In addition, immunization intervals are not particularly limited, and the immunization is carried out 1 to 10 times, and more preferably 2 to 5 times, at intervals of several days to several weeks, and preferably at intervals of 2 to 5 weeks. Thereafter, one to sixty days, and preferably one to fourteen days after the final immunization, antibody-producing cells are collected. Examples of the antibody-producing cells include splenic cells, lymph node cells, and peripheral blood cells. Among these cells, splenic cells or local lymph node cells are preferable.

To obtain cell fusion hybridomas, cell fusion of antibody-producing cells with myeloma cells is carried out. As myeloma cells to be fused with antibody-producing cells, commercially available cells that have been established from animals such as mice can be used. As an established cell line used herein, a cell line, which has drug selectivity, cannot survive in a HAT selection medium (containing hypoxanthine, aminopterin and thymidine) in an unfused state, and can survive therein only in a state in which it is fused with antibody-producing cells, is preferable. Examples of the myeloma cells include mouse myeloma cell lines such as P3X63-Ag.8.U1 (P3U1) or NS-1.

Subsequently, the aforementioned myeloma cells are fused with antibody-producing cells. For cell fusion, antibody-producing cells ($1\times10^6$ to $1\times10^7$ cells/ml) are mixed with myeloma cells ($2\times10^5$ to $2\times10^6$ cells/ml) in an animal cell culture medium containing no serum, such as DMEM or a RPMI-1640 medium (wherein the cell ratio between the antibody-producing cells and the myeloma cells is preferably 5:1), and a fusion is then carried out in the presence of a cell fusion promoter. As a cell fusion promoter, polyethylene glycol with a mean molecular weight of 1000 to 6000 Daltons or the like can be used. In addition, antibody-producing cells may also be fused with myeloma cells using a commercially available cell fusion apparatus that utilizes electrical stimulation (e.g. electroporation).

After completion of the cell fusion treatment, hybridomas of interest are selected from the resulting cells. As a selection method, a cell suspension is appropriately diluted, for example, with a fetal bovine serum-containing RPMI-1640 medium, and the resulting cell suspension is inoculated at a cell density of approximately $3\times10^5$ cells/well on a microtiter plate. Thereafter, a selection medium is added to each well, and a culture is then carried out, while exchanging the selection medium with a fresh one, as appropriate. As a result, cells growing approximately 14 days after initiation of the culture in the selection medium can be obtained as hybridomas.

Thereafter, the presence or absence of an antibody of interest in a culture supernatant of the growing hybridomas is screened. The screening of hybridomas may be carried out according to an ordinary method, and the type of the screening method is not particularly limited. For instance, an aliquot of the culture supernatant of the growing hybridomas contained in the well is collected, and it is then subjected to enzyme immunoassay, radioimmunoassay or the like, so that hybridomas that produce an antibody binding to CDH3 can be screened. The fused cells are cloned according to limiting dilution or the like, and thus, hybridomas can be finally established as cells that produce a monoclonal antibody.

As a method of collecting a monoclonal antibody from the established hybridomas, an ordinary cell culture method, an ascites extraction method or the like can be adopted. In the cell culture method, hybridomas are cultured in an animal cell culture medium, such as a 10% fetal bovine serum-containing RPMI-1640 medium, an MEM medium or a serum-free medium, under common culture conditions (e.g. 37° C. and 5% $CO_2$) for 7 to 14 days, and thereafter, an antibody is obtained from the culture supernatant.

In the ascites extraction method, approximately $1\times10^7$ hybridomas are administered into the abdominal cavity of an animal of the same species as a mammal, from which the myelomas have been obtained, so as to allow large quantities of hybridomas to grow therein. Then, one or two weeks later, ascites is collected. When purification of an antibody is required in the aforementioned antibody collection methods, known methods, such as ammonium sulfate precipitation, ion exchange chromatography, gel filtration and affinity chromatography, are selected as appropriate, or these methods are used in combination, so as to purify the antibody.

The type of the antibody of the present invention is not particularly limited. Any one of a mouse antibody, a human antibody, a rat antibody, a rabbit antibody, a sheep antibody, a camel antibody, a bird antibody and the like, or recombinant antibodies that have been artificially modified for purposes such as a reduction in heterogenic antigenicity to humans, such as a chimeric antibody or a humanized antibody, may be employed. The recombinant antibody can be produced by known methods. The chimeric antibody is an antibody consisting of the variable regions of the heavy and light chains of an antibody from a mammal other than a human, such as a mouse antibody, and the constant regions of the heavy and light chains of a human antibody. Such a chimeric antibody can be obtained by ligating DNA encoding the variable region of a mouse antibody to the DNA encoding the constant region of a human antibody, then inserting this ligate into an expression vector, and then introducing the vector into a host, so that the chimeric antibody can be generated. A humanized antibody is obtained by transplanting the complementarity determining region (CDR) of an antibody from a mammal other than a human, such as a mouse antibody, into the complementarity determining region of a human antibody, and a general recombination technique has been known. Specifically, a DNA sequence designed to ligate the CDR of a mouse antibody to the framework region (FR) of a human antibody is synthesized from several oligonucleotides produced to have some overlapped portions at the termini thereof according to a PCR method. The obtained DNA is ligated to DNA encoding the constant region of a human antibody, and the thus ligated DNA is then inserted into an expression vector. This expression vector is introduced into a host, so that a humanized antibody can be generated (EP239400, International Publication Among host cell systems used for protein expression, many antibody-producing host cell systems are derived from mammals. The manufacturers may preferentially determine a specific host cell system most suitable for a gene product to be expressed. Examples of a common host cell system include, but are not limited to, a CHO-derived cell line (a Chinese hamster ovary cell line), CV1 (a monkey kidney system), COS (a derivative of CV1 to an SV40T antigen), SP2/0 (mouse myelomas), P3x63-Ag3.653 (mouse myelomas), 293 (human kidney), and 293T (a derivative of 293 to an SV40T antigen). Such a host cell system is available from commercial facilities or the American Tissue Culture Collection (ATCC), or also from institutions that have published some publications.

Preferably, the host cell system is either a CHO-derived cell line comprising defective expression of a dgfr gene, or SP2/0. (see Urland, G et al., Effect of gamma rays at the dihydrofolate reductase locus: deletions and inversions, Somat. Cell. Mol. Genet. Vol. 12, 1986, pp. 5555-566, and Schulman, M. et al., A better cell line for making hybridomas secreting specific antibodies, Nature Vol. 276, 1978, pp. 269-270, respectively.) Most preferably, the host cell system is DHFR-deficient CHO.

Transfection of a plasmid into a host cell can be achieved by any given technique. Specific examples of such a transfection method include, but are not limited to, transfection (including a calcium phosphate method, a DEAE method, lipofection, and electroporation), a method of introducing DNA utilizing an envelope such as Sendai virus, microinjection, and infection using viral vectors such as retrovirus or adenovirus. (see Current Protocols in Molecular Biology, Chapter 9 Introduction of DNA into Mammalian Cells, John Wiley and Sons, Inc.) Introduction of a plasmid into a host by electroporation is most preferable.

Moreover, a method of obtaining a human antibody has also been known. For example, human lymphocytes are sensitized with a desire antigen or a cell expressing such a desired antigen in vitro, and the sensitized lymphocytes are then fused with human myeloma cells, such as U266, so as to obtain a desired human antibody having an activity of binding to an antigen (see JP Patent Publication (Kokoku) No. 1-59878 B (1989)). Also, a desired human antibody can be obtained by immunizing a transgenic animal having all repertoires of human antibody genes with a desired antigen (see WO93/12227, WO92/03918, WO94/02602, WO94/25585, WO96/34096, and WO96/33735). Moreover, a technique of obtaining a human antibody by panning using a human antibody library has also been known. For example, the variable region of a human antibody used as a single-chain antibody (scFv) is allowed to express on the surface of phages according to a phage display method, and a phage binding to an antigen can be then selected. By analyzing the selected phage gene, a DNA sequence encoding the variable region of a human antibody binding to the antigen can be determined If the DNA sequence of the scFv binding to the antigen could be determined, it would be possible to produce a suitable expression vector based on the determined sequence and to obtain a human antibody using the expression vector. These methods have already been well known, and WO92/01047, WO92/20791, WO93/06213, WO93/11236, WO93/19172, WO95/01438, and WO95/15388 can be referred.

These antibodies may be any one of a monovalent antibody, a divalent antibody and a polyvalent antibody, as long as they are capable of recognizing CDH3. The antibodies may also be low-molecular-weight antibodies such as an antibody fragment, or modified antibodies. Moreover, the antibodies may also be antibody fragments or low-molecular-weight antibodies, such as Fab, Fab', F(ab')$_2$, Fv, ScFv (single chain Fv) or Diabody, with which an Fc portion is fused. In order to obtain such antibodies, genes encoding these antibodies may be constructed, and they may be then each introduced into expression vectors, and they may be then allowed to express in suitable host cells.

It is also possible to bind various types of molecules such as polyethylene glycol (PEG) to these antibodies and then to use them. Such modified antibodies can be obtained by performing a chemical modification on the obtained antibody. It is to be noted that the method of modifying antibodies is known to a person skilled in the art.

In the immune complex of the present invention, a chemotherapeutic agent is allowed to further bind to the aforementioned antibody, so that the immune complex can be used as a cytotoxic agent. The immune complex of the present invention is allowed to come into contact with, for example, cancer cells that express CDH3, so as to damage the cancer cells.

A preferred embodiment of the immune complex of the present invention includes what is called ADC, in which a cytotoxic substance such as a drug is bound to an antibody.

Examples of the chemotherapeutic agent used in the present invention include duocarmycin, analogs and derivatives of duocarmycin, CC-1065, duocarmycin analogs comprising CBI as a main ingredient, duocarmycin analogs comprising MCBI as a main ingredient, duocarmycin analogs comprising CCBI as a main ingredient, doxorubicin, doxorubicin conjugates, morpholino-doxorubicin, cyano-morpholino-doxorubicin, dolastatin, dolastatin-10, combretastatin, calicheamicin, maytansine, maytansine analogs, DM1, DM2, DM3, DM4, DMI, auristatin E, auristatin EB (AEB), auristatin EFP (AEFP), monomethyl auristatin E (MMAE), monomethyl auristatin F (MMAF), 5-benzoyl valeric acid AE ester (AEVB), tubulysin, disorazole, epothilone, paclitaxel, docetaxel, SN-38, topotecan, rhizoxin, echinomycin, colchicine, vinblastine, vindesine, estramustine, cemadotin, eryuterobin, methotrexate, methopterin, dichloromethotrexate, 5-fluorouracil, 6-mercaptopurine, cytosine arabinoside, melphalan, ryuroshin, Liu rosiglitazone Dine, actinomycin, daunorubicin, daunorubicin conjugates, mitomycin C, mitomycin A, carminomycin, aminopterin, tallysomycin, podophyllotoxin, podophyllotoxin derivatives, etoposide, etoposide phosphate, vincristine, taxol, taxol taxotere retinoic acid, butyric acid, N$^8$-acetyl spermidine and camptothecin, but the examples are not limited thereto.

The ADC of the present invention can be produced by binding the above-described chemotherapeutic agent to an antibody according to a known method. The antibody may be directly bound to the chemotherapeutic agent via their linking group or the like, or they may be indirectly bound to each other via a linker or another substance.

Examples of the linking group used when the chemotherapeutic agent is directly bound to the antibody include a disulfide bond using an SH group and a bond mediated by maleimide. For instance, an intramolecular disulfide bond in the Fc region of the antibody and the disulfide bond of a drug are reduced, and they are then bound to each other via a disulfide bond. Moreover, there is also a method involving mediation of maleimide. Furthermore, as an alternative method, there is also a method of introducing cysteine into an antibody by genetic technology.

It is also possible to indirectly bind the antibody to the chemotherapeutic agent via another substance (linker). The linker desirably has one or two or more types of functional groups that react with the antibody, or with the chemotherapeutic agent, or with both of them. Examples of such a functional group include an amino group, a carboxyl group, a mercapto group, a maleimide group, and a pyridinyl group.

Examples of the linker include N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimide butyric acid N-succinimidyl ester (GMBS), ε-maleimidocaproic acid N-hydroxysuccinimide ester (EMCS), m-maleimide benzoyl-N-hydroxysuccinimide ester (MBS), N-(α-maleimidoacetoxy)-succinimide ester (AMAS), succinimidyl-6-(β-maleimidopropionamide)hexanoate (SMPH), N-succinimidyl 4-(p-maleimidophenyl)butyrate (SMPB), N-(p-maleimidophenyl)isocyanate (PMPI), 6-maleimidocaproyl (MC), maleimidopropanoyl (MP), p-aminobenzyloxycarbonyl (PAB), N-succinimidyl 4(2-pyridylthio)pentanoate (SPP). N-succinimidyl(4-iodo-acetyl)aminobenzoate (STAB), and N-succinimidyl (4-(2-pyridylthio)butanoate (SPDB), but the examples are not limited thereto. In addition, this linker may be a peptide linker such as valine-citrulline (Val-Cit) or alanine-phenylalanine (ala-phe), or the aforementioned linkers may be combined with one another, as appropriate, and may be then used.

With regard to the method of binding a chemotherapeutic agent to an antibody, binding can be carried out according to the methods described, for example, in Cancer Research; 68 (22) 9280 (2008), Nature Biotechnology; 26(8) 925 (2008), Bio Conjugate Chemistry; 19, 1673 (2008), Cancer Research; 68 (15) 6300 (2008), or JP Patent Publication (Kohyo) No. 2008-516896 A.

Another embodiment of the present invention includes what is called immunotoxin, in which a toxin is bound to an antibody in a chemical or genetic technology.

Examples of the toxin used in the present invention include diphtheria toxin A chain, Pseudomonas endotoxin, ricin chain, deglycosylated ricin A chain, gelonin, and saporin.

Since the immune complex of the present invention exhibits high cellular cytotoxicity, it can be used as a cytotoxic agent. Moreover, the antibody of the present invention can be used as a therapeutic agent for diseases, in which CDH3 is highly expressed. The cytotoxic agent and therapeutic agent for such CDH3 highly expressing diseases of the present invention are able to damage cancer cells by allowing them to come into contact with, for example, cancer cells that express cadherin. Examples of the human CDH3 highly expressed disease include colorectal cancer, non-small-cell lung cancer, breast cancer, cancer of the head and neck, ovarian cancer, lung cancer, invasive bladder cancer, pancreatic cancer, metastatic brain tumor, thyroid cancer, squamous cell carcinoma of the head and neck, squamous cell carcinoma of the esophagus, squamous cell carcinoma of the lung, squamous cell carcinoma of the skin, melanoma, mammary cancer, pulmonary adenocarcinoma, squamous cell carcinoma of the uterine cervix, squamous cell carcinoma of the pancreas, squamous cell carcinoma of the colon, squamous cell carcinoma of the stomach, prostatic cancer, osteosarcoma, and soft tissue sarcoma.

The immune complex of the present invention is appropriately combined with a pharmaceutically acceptable carrier, excipient, diluent and the like, as necessary, so that it can be used as a pharmaceutical composition. The pharmaceutical composition of the present invention can be formulated in the form of an injection, for example. The administration amount of the pharmaceutical composition of the present invention depends on the degree of symptoms, age and body weight of a patient, administration method, and the like. The weight of the antibody serving as an active ingredient is generally in the range of approximately 10 ng to approximately 100 mg/kg body weight.

The present invention will be more specifically described in the following examples. However, these examples are not intended to limit the scope of the present invention.

EXAMPLES

Example 1

Establishment of CDH3-Expressing CHO Cell Line

In order to obtain a cell line used in screening for an anti-CDH3 antibody, CHO cells expressing the full-length CDH3 were established.
(1) Construction of CDH3 Gene Expression Vector In order to insert the full-length human CDH3 DNA shown in SEQ ID NO. 1 into a mammalian expression vector pEF4/myc-HisB (Invitrogen), the DNA was digested with two types of restriction enzymes, KpnI (TAKARA BIO INC.) and XbaI (TAKARA BIO INC.), at 37° C. for 1 hour. Thereafter, the resulting DNA was inserted into the pEF4/myc-HisB that had also been digested with KpnI and XbaI according to an ordinary method using T4 DNA ligase (Promega), thereby obtaining an expression vector, pEF4-CDH3-myc-His.
(2) Obtainment of CDH3 Stable Expression Cell Line On the day before transfection, CHO cells ($8 \times 10^5$) were inoculated on a dish with a diameter of 10 cm in accordance with the protocols included with FuGENE (registered trademark) 6 Transfection Reagent (Roche Diagnostics), and they were then cultured overnight. Thereafter, 8 μg of the expression vector pEF4-CDH3-myc-His and 16 μL of the FuGENE 6 reagent were mixed into 400 μL of a serum-free RPMI1640 medium (SIGMA-ALDRICH), and the obtained mixture was then left at room temperature for 15 minutes. Thereafter, the mixture was added to the cell culture, so as to perform transfection. Two days after the transfection, cloning was carried out by limiting dilution using a selective reagent (Zeocin (registered trademark)).

The cloning and selection of CDH3 full-length expression CHO were carried out by a Western blotting method using Anti-c-Myc Monoclonal Antibody (SANTA CRUZ BIOTECHNOLOGY). As a result, a CDH3 full-length expression CHO cell line (EXZ1501) having a high expression level and a high growth rate was obtained. The measurement results obtained by examining the reactivity of this cell line with a commercially available anti-CDH3 antibody (R & D SYSTEMS) by flow cytometry are shown in FIG. 1.

Example 2

Preparation of Soluble CDH3 Antigen

In order to be used as an immunogen in the production of an anti-CDH3 antibody, a soluble CDH3 (sCDH3) protein, in which its C-terminal transmembrane region and the subsequent regions were deleted, was prepared.
(1) Construction of Soluble CDH3 Antigen Expression Vector Using full-length CDH3 cDNA as a template, a PCR reaction was carried out employing a forward primer (SEQ ID NO. 3: CGCGGTACCATGGGGCTCCCTCGT) and a reverse primer (SEQ ID NO. 4: CCGTCTAGATAACCTC-CCTTCCAGGGTCC) that had been designed to amplify a region corresponding to the CDH3 extracellular region (which corresponded to positions 1-654 of SEQ ID NO. 2; hereinafter referred to as "sCDH3 cDNA"). KOD-Plus (Toyobo Co., Ltd.) was used in the reaction, and the reaction was carried out under reaction conditions consisting of 30 cycles of 94° C.—15 seconds, 55° C.—30 seconds, and 68° C.—90 seconds.

Thereafter, a gel fragment containing an approximately 2.0-kbp band that was a size of interest was cut out in agarose gel electrophoresis, and using QIA (registered trademark) Quick Gel Extraction Kit (QIAGEN), sCDH3 cDNA of interest was obtained.

In order to insert this sCDH3 cDNA into an expression vector pEF4/myc-HisB, the DNA was digested with two types of restriction enzymes KpnI and XbaI, and it was then inserted into pEF4/myc-HisB that had also been digested with KpnI and XbaI according to an ordinary method using T4 DNA ligase, so as to obtain an expression vector pEF4-sCDH3-myc-His.
(2) Expression of Soluble CDH3 Protein On the day before transfection, CHO cells ($8 \times 10^5$) were inoculated on a dish with a diameter of 10 cm in accordance with the protocols included with the FuGENE 6 Transfection Reagent, and they were then cultured overnight. Thereafter, 8 μg of the expression vector pEF4-CDH3-myc-His and 16 μL of the FuGENE 6 reagent were mixed into 400 μL of a serum-free RPMI1640 medium (SIGMA-ALDRICH), and the obtained mixture was then left at room temperature for 15 minutes. Thereafter, the mixture was added to the cell culture, so as to perform transfection. Two days after the transfection, cloning was carried out by limiting dilution using a selective reagent (Zeocin).

Soluble CDH3-expressing CHO cells were selected according to a Western blot method using an anti-c-Myc monoclonal antibody (SANTA CRUZ BIOTECHNOLOGY). It was attempted to select a cell line, which was able to secrete a large amount of soluble CDH3 into the culture supernatant and which was able to grow favorably. As a result, a soluble CDH3-expressing CHO cell line (EXZ1702) was obtained. Using three roller bottles each having a culture area of 1,500 cm$^2$, the selected soluble CDH3-expressing CHO cell line (EXZ1702) was cultured for 72 hours in 333 mL of a serum-free medium CHO-S-SFM-II (Invitrogen) per roller bottle. Thereafter, a culture supernatant was recovered. A soluble CDH3 protein was obtained from the recovered culture supernatant according to affinity chromatography using HisTrap (registered trademark) HP column (GE Healthcare Biosciences) and gel filtration chromatography using Superdex (registered trademark) 200 pg column (GE Healthcare Biosciences).

Example 3

Production of Anti-CDH3 Monoclonal Antibody (1) Production of Monoclonal Antibody using Soluble CDH3 Protein as Immunogen 50 μg of a soluble CDH3 protein dissolved in a normal saline and Titer-MAX Gold (registered trademark) (Titer-Max) were mixed in equal volumes. The obtained mixture was injected into the abdominal cavity and subcutis of each MRL/lpr mouse (Japan SLC, Inc.), so as to carry out initial immunization The second immunization and the subsequent immunizations were carried out by mixing a soluble CDH3 protein (protein amount: 25 μg) that had been prepared in the same manner as described above with Titer-MAX gold and then injecting the obtained mixture into the abdominal cavity and subcutis of the mouse. Three days after the final immunization, splenic cells were aseptically prepared from the mouse, and the splenic cells were then fused with mouse myeloma cells SP2/O-Ag14 or P3-X63-Ag8.653 according to an ordinary method (polyethylene glycol method).
(2) Selection of Anti-CDH3 Antibody-Producing Hybridomas An anti-CDH3 antibody was selected by flow cytometry using a CHO cell line (EXZ1501) expressing full-length CDH3.

Specifically, the CHO cell line (EXZ1501) that expressed full-length CDH3 was treated with 2 mM EDTA-PBS, so that it was removed from the culture plate. Thereafter, the cells were suspended in a FACS solution to a cell density of 1×10$^6$ cells/mL. This cell suspension was inoculated on a 96-well plate to an amount of 50 μL/well, and a culture supernatant of hybridomas was then added thereto, so that they were reacted at 4° C. for 60 minutes. Thereafter, the reaction solution was washed with a FACS solution (200 μL/well) two times, and AlexaFluor 488-labeled anti-mouse IgG-goat F(ab')$_2$ (Invitrogen) was then added. Then, the mixture was reacted at 4° C. for 30 minutes. Thereafter, the reaction solution was washed with a FACS solution two times, and it was then subjected to flow cytometry, so as to select hybridomas that were reacted with the CDH3-expressing CHO cells.

Typical reaction results obtained from the reactions of an antibody obtained from the aforementioned hybridomas with CDH3-expressing CHO cells (EXZ1501), with CHO cells as a parent cell line, and with a human bronchioalveolar carcinoma cell line NCI-H358 are shown in FIG. 2. It was confirmed that all of the selected hybridomas reacted with CDH3-expressing CHO cells (EXZ 1501) and NCI-H358, and did not react with CHO cells.

Example 4

Expression of CDH3 mRNA in Normal Tissues and Cancer Tissues

Samples were recovered from normal human tissues and various types of cancer tissues according to laser capture microdissection, and total RNA was then prepared from each sample according to an ordinary method using ISOGEN (NIPPON GENE CO., LTD.). 10 ng each of RNA was subjected to gene expression analysis in accordance with Expression Analysis Technical Manual (Affymetrix) using GeneChip U-133B (Affymetrix). The mean value of the expression scores of all genes was set at 100, and genes whose expression had been increased in cancer cells were then searched. As a result, it was found that the expression of CDH3 had a certain limit in normal human tissues, and that CDH3 was highly expressed in lung cancer, colon cancer, and pancreatic cancer (FIGS. 3A and 3B). Moreover, the expression of CDH3 mRNA was examined in several pancreatic cancer tissues having different degrees of differentiation. As a result, regardless of the degree of differentiation, tissues in which high expression of CDH3 mRNA was observed were found (FIG. 3C).

Example 5

Expression of CDH3 Protein in Cancer Tissues Observed according to Immunohistochemical Staining In order to confirm the expression of the CDH3 protein in clinical cancer specimens, immunostaining was carried out using cancer specimen tissue arrays.

As such cancer specimen tissue arrays, pancreatic cancer (adenocarcinoma), lung cancer (adenocarcinoma), lung cancer (squamous cell carcinoma), and colon cancer (adenocarcinoma), manufactured by Shanghai Outdo Biotech Co., Ltd., were used.

A slide of each tissue array was subjected to a deparaffinization treatment, and was then activated in 10mM Tris 1mM EDTA (pH 9.0) at 95° C. for 40 minutes. Endogenous peroxidase was deactivated using a blocking reagent included with ENVISION+ Kit (Dako), and it was then reacted with an anti-CDH3 antibody 610227 (BD BIOSCIENCE) and with an anti-HBs antibody Hyb-3423 used as a negative control in a concentration of 5 μg/mL at 4° C. overnight. Thereafter, the antibody solution was washed out, and the reaction solution was then reacted with a polymer secondary antibody reagent included with ENVISION+ Kit at room temperature for 30 minutes. Thereafter, color development was carried out with a coloring reagent included with ENVISION+ Kit, and nuclear staining was then performed with a hematoxylin-eosin solution.

The results are shown in FIG. 4. Cancer cells were stained with the anti-CDH3 antibody, but normal cells were not stained therewith.

Example 6

Purification of RNA from Hybridomas

Cytoplasmic RNA was isolated from mouse hybridoma cells producing the CDH3 antibody according to the method described in Gough, Rapid and quantitative preparation of cytoplasmic RNA from small numbers of cells, Analytical Biochemisty, 173, pp. 93-95 (1988) (wherein another TNE buffer (25 mM Tris-HC1, pH 7.5; 1% NP-40; 150 mM NaCl; 1 mM EDTA, pH 8.0) was used in the present operation, instead of the lysis buffer described in the aforementioned study paper). As a specific operation procedure, hybridoma cells ($5 \times 10e^6$) was suspended in 0.2 mL of a TNE buffer to dissolve the cell membrane therein, and the cell nucleus was then removed by centrifugation. To approximately 0.2 mL of the obtained cytoplasm supernatant, 0.2 mL of an extraction buffer (10 mM Tris-HCl, pH 7.5; 0.35 M NaCl; 1% (w/v) SDS; 10 mM EDTA, pH 8.0; 7 M urea) was added. The obtained mixture was extracted with phenol and chloroform, and glycogen (Roche; Cat No. 901393) was then added as a carrier to the obtained RNA solution. The mixture was precipitated with ethanol. Subsequently, 10 to 50 μl of sterile distilled water was added to the RNA precipitate, resulting in a cytoplasmic RNA concentration of 0.5 to 2 μg/μl, so that the precipitate was dissolved therein.

Example 7

Production of cDNA Library from RNA Prepared from Hybridomas

In order to synthesize single-stranded cDNA, 0.5 to 3 μg of the above-prepared cytoplasmic RNA was added to a reaction solution containing 50 mM Tris-HCl, pH 8.3 (room temperature); 75 mM KCl; 3 mM $MgCl_2$; 10 mM DTT, 100 ng of random primer, 0.5 mM dNTP, and 200 units of Superscript II (reverse transcriptase, Invitrogen) to prepare 20 μL of a reaction mixture, and the reaction mixture was then incubated at 42° C. for 50 minutes. The thus synthesized cDNA library was directly used as a template in a polymerase chain reaction (PCR) method.

Example 8

Amplification of Gene Encoding Variable Region of Anti-CDH3 Antibody by PCR Method Primers used in the experiments were all synthesized by Hokkaido System Science Co., Ltd.
A. Primers Used to Amplify Gene Encoding Variable Region of Mouse Light Chain by PCR Method Using two types of primer sets, namely, (1) a DNA primer having homology with a FR1 portion at the 5'-terminus, and 4 primer sets having homology with a J chain gene in a mouse L chain at the 3'-terminus, and (2) primer sets having homology with an L chain signal portion at the 5'-terminus (7 primer sets), and a primer with a KC portion at the 3'-terminus (KVL antisense primer), mouse immunoglobulin L chain variable region DNA was isolated from the cDNA by a polymerase chain reaction. The primer sequences are as follows.
(1) 4 Sense Primer Sets for Cloning of Mouse L Chain Variable Region With reference to "Phage Display—A Laboratory Manual—, Barbas Burton Scott Silverman" PROTOCOL 9.5, 17 types of sense primers and 3 types of reverse primers were synthesized by Hokkaido System Science Co., Ltd.

VK sense (FR1 portion): A mixture of the following 17 primers was used as a VK sense primer.

```
                                            SEQ ID NO. 5
5'-GAYATCCAGCTGACTCAGCC-3' (Degeneracy 2):

SEQ ID NO. 6
5'-GAYATTGTTCTCWCCCAGTC-3' (Degeneracy 4):

SEQ ID NO. 7
5'-GAYATTGTGMTMACTCAGTC-3' (Degeneracy 8):

SEQ ID NO. 8
5'-GAYATTGTGYTRACACAGTC-3' (Degeneracy 8):

SEQ ID NO. 9
5'-GAYATTGTRATGACMCAGTC-3' (Degeneracy 8):

SEQ ID NO. 10
5'-GAYATTMAGATRAMCCAGTC-3' (Degeneracy 16):

SEQ ID NO. 11
5'-GAYATTCAGATGAYDCAGTC-3' (Degeneracy 12):

SEQ ID NO. 12
5'-GAYATYCAGATGACACAGAC-3' (Degeneracy 4):

SEQ ID NO. 13
5'-GAYATTGTTCTCAWCCAGTC-3' (Degeneracy 4):

SEQ ID NO. 14
5'-GAYATTGWGCTSACCCAATC-3' (Degeneracy 8):

SEQ ID NO. 15
5'-GAYATTSTRATGACCCARTC-3' (Degeneracy 16):

SEQ ID NO. 16
5'-GAYRTTKTGATGACCCARAC-3' (Degeneracy 16):

SEQ ID NO. 17
5'-GAYATTGTGATGACBCAGKC-3' (Degeneracy 12):

SEQ ID NO. 18
5'-GAYATTGTGATAACYCAGGA-3' (Degeneracy 4):

SEQ ID NO. 19
5'-GAYATTGTGATGACCCAGWT-3' (Degeneracy 4):

SEQ ID NO. 20
5'-GAYATTGTGATGACACAACC-3' (Degeneracy 2):

SEQ ID NO. 21
5'-GAYATTTTGCTGACTCAGTC-3' (Degeneracy 2):
```

J Antisense (4 Primer Sets)

```
J1/J2 antisense primer (1)
                                            SEQ ID NO. 22
5'-GGSACCAARCTGGAAATMAAA-3' (Degeneracy 8):

J4 antisense primer (2)
                                            SEQ ID NO. 23
5'-GGGACAAAGTTGGAAATAAAA-3':

J5 antisense primer (3)
                                            SEQ ID NO. 24'
5'-GGGACCAAGCTGGAGCTGAAA-3':
```

A mixture of J1/J2, J4, and J5 antisense primers (4)
(2) 7 Primer Sets for Cloning of Mouse L Chain Variable Region
VK Sense (Signal Peptide Portion)

These primers were prepared by modifying the nucleotide sequences based on the Mouse Ig-Primer Set of Novagen (Novagen; Merck, Cat. No. 69831-3), such that restriction sites were removed.

```
Sense primer set A
                                    SEQ ID NO. 25
5'-ATGRAGWCACAKWCYCAGGTCTTT-3':

Sense primer set B
                                    SEQ ID NO. 26
5'-ATGGAGACAGACACACTCCTGCTAT-3':

Sense primer set C
                                    SEQ ID NO. 27
5'-ATGGAGWCAGACACACTSCTGYTATGGGT-3':

Sense primer set D (a mixture of the following
two types of primers was used)
                                    SEQ ID NO. 28
5'-ATGAGGRCCCCTGCTCAGWTTYTTGGIWTCTT-3':

SEQ ID NO. 29
5'-ATGGGCWTCAAGATGRAGTCACAKWYYCWGG-3':

Sense primer set E (a mixture of the following
three types of primers was used)
                                    SEQ ID NO. 30
5'-ATGAGTGTGCYCACTCAGGTCCTGGSGTT-3':

SEQ ID NO. 31
5'-ATGTGGGGAYCGKTTTYAMMCTTTTCAATTG-3':

SEQ ID NO. 32
5'-ATGGAAGCCCCAGCTCAGCTTCTCTTCC-3':

Sense primer set F (a mixture of the following
four types of primers was used)
                                    SEQ ID NO. 33
5'-ATGAGIMMKTCIMTTCAITTCYTGGG-3':

SEQ ID NO. 34
5'-ATGAKGTHCYCIGCTCAGYTYCTIRG-3':

SEQ ID NO. 35
5'-ATGGTRTCCWCASCTCAGTTCCTTG-3':

SEQ ID NO. 36
5'-ATGTATATATGTTTGTTGTCTATTTCT-3':

Sense primer set G (a mixture of the following
four types of primers was used)
                                    SEQ ID NO. 37
5'-ATGAAGTTGCCTGTTAGGCTGTTGGTGCT-3':

SEQ ID NO. 38
5'-ATGGATTTWCARGTGCAGATTWTCAGCTT-3':

SEQ ID NO. 39
5'-ATGGTYCTYATVTCCTTGCTGTTCTGG-3':

SEQ ID NO. 40
5'-ATGGTYCTYATVTTRCTGCTGCTATGG-3':

KVL antisense primer
                                    SEQ ID NO. 41
5'-ACTGGATGGTGGGAAGATGGA-3':
```

B. Primers Used to Amplify Gene Encoding Mouse H Chain V Region by PCR Method

Using a primer having homology with a mouse H chain signal portion (4 primer sets) at the 5'-terminus and a primer having homology with a KC portion at the 3'-terminus, or using 1 primer set having homology with a FR1 portion at the 5'-terminus and two types of primer sets having homology with the constant region of a mouse H chain (IGHC) at the 3'-terminus, mouse immunoglobulin H chain variable region DNA was isolated from the cDNA by a polymerase chain reaction. The primer sequences are as follows.

(3) Primers for Cloning of Mouse H Chain Variable Region VH Sense (Signal Portion: 4 Primer Sets)

These primers were designed with reference to Table 2.12.2 shown in Current Protocols in Immunology (John Wiley and Sons, Inc.), Unit 2.12 Cloning, Expression, and Modification of Antibody V Regions.

```
                                    SEQ ID NO. 42
5'-ATGGRATGSAGCTGKGTMATSCTCTT-3' (Degeneracy 32):

SEQ ID NO. 43
5'-ATGRACTTCGGGYTGAGCTKGGTTTT-3' (Degeneracy 8):

SEQ ID NO. 44
5'-ATGGCTGTCTTGGGGCTGCTCTTCT-3':

SEQ ID NO. 45
5'-ATGGRCAGRCTTACWTYY-3' (Degeneracy 32):
```

(4) Primers for Cloning of Mouse H Chain Variable Region VH Sense (FR1 Portion)

This primer was designed by modifying the nucleotide sequence of the sense primer described in Tan et al., "Superhumanized" Antibodies: Reduction of Immunogenic Potential by Complementarity-Determining Region Grafting with Human Germline Sequences: Application to an Anti-CD281, Journal of Immunology 169 (2002) pp. 1119-1125.

```
                                    SEQ ID NO. 46
5'-SAGGTSMARCTKSAGSAGTCWGG-3' (Degeneracy 256):
```

VH Antisense (Antisense Primer Common in 3 and 4)

This primer was designed by degenerating the nucleotide sequence such that it can anneal with all isoforms of mouse IgG

```
                                    SEQ ID NO. 47
5'-CASCCCCATCDGTCTATCC-3' (Degeneracy 6):
```

Example 9

Construction of Transient Expression Vector for Chimeric Anti-CDH3 Immunoglobulin Production of Expression Plasmid:

Using the primers shown in Example 8, a variable region in each of the L chain and H chain of an anti-CDH3 mouse monoclonal antibody was amplified by a PCR method employing DNA Engine (Peltier Thermal Cycler, MJ Research, Bio-Rad). The amplified DNA fragment was inserted into a subcloning vector pGEM (Promega), and the nucleotide sequence thereof was then determined using T7, SP6 universal primers.

Among the nucleotide sequences determined in Example 9, sequences, in which a portion corresponding to CDR was converted to amino acids, are shown in Table 1.

TABLE 1

| Amino acid sequences corresponding to sequence numbers ||
| --- | --- |
| SEQ ID NO. | Amino acid sequence |
| 48 | DYNID |
| 49 | SYGVH |
| 50 | GYYMH |
| 51 | AYNMH |
| 52 | DYNMD |

TABLE 1 -continued

Amino acid sequences corresponding to sequence numbers

| SEQ ID NO. | Amino acid sequence |
|---|---|
| 53 | DHNID |
| 54 | TYWIY |
| 55 | SYWMN |
| 56 | YIFPNNGGFGYNQKFKN |
| 57 | FIDPYSGIITYNQTFKG |
| 58 | VIWAGGNTIYNSALMS |
| 59 | EINPSTGGTTYNQKFKA |
| 60 | YIFPNNGGAGYNPKFKN |
| 61 | YIYPSNGGTGYNQKFKN |
| 62 | EIDPSDNYTYYSQKFKG |
| 63 | RIHPSDSETHYNQKFKS |
| 64 | VIWSGGSTDYNAAFIS |
| 65 | PYGNYDYYYAMDY |
| 66 | NSNNGFAY |
| 67 | RGYYDGGFDY |
| 68 | PHYGDYAGFYALDH |
| 69 | DSNYVGFAF |
| 70 | KMEAYYSYDYYYAMDY |
| 71 | PYGNDDYYYAMDY |
| 72 | RHWDGFAY |
| 73 | WDYDHFDY |
| 74 | SASSSVSSGNFH |
| 75 | RASKSISKYLA |
| 76 | RTSENIYSNLA |
| 77 | RASQDISNYLN |
| 78 | RASQDITNYLN |
| 79 | RASKRISKYLA |
| 80 | SASSSVSSRYLH |
| 81 | RTSNLAS |
| 82 | SGSTLQS |
| 83 | YTSRLHS |
| 84 | AAKNLAD |
| 85 | GTSNLAS |
| 86 | QQHYEYPYT |
| 87 | QQYSKFPRT |
| 88 | QQDSKHPRT |
| 89 | QHFYDTPWT |

TABLE 1 -continued

Amino acid sequences corresponding to sequence numbers

| SEQ ID NO. | Amino acid sequence |
|---|---|
| 90 | QQHNEYPWT |
| 91 | QQYNEYPYT |
| 92 | QQYYEYPYT |
| 93 | QQWSGYPPT |
| 94 | QPYHSDPFT |

The nucleotide sequence of a variable region in each of the L chain and H chain of the chimeric anti-CDH3 antibody was searched on the IMGT/V-QUEST Search page (world wide web at imgt.cines.fr/IMGT_vquest/vquest?livret=0&Option =mouselg). As a result, it was confirmed that the antibody gene could be reliably cloned. Subsequently, genes each encoding the V regions of the L chain and H chain of the cloned anti-CDH3 antibody were prepared by designing a gene, in which a gene encoding a human Ck region was connected with a chimeric L chain expression vector and a gene encoding a human Cg1 region was connected with a chimeric H chain expression vector, and then performing the artificial synthesis of the thus designed, full-length L chain and H chain chimeric antibody genes by GenScript. Upon the artificial synthesis of the full-length genes, optimization of codon usage was carried out for the advantages of gene expression in CHO-producing cells (in accordance with the method described in Kim et al., Codon optimization for high-level expression of human erythropoietin (EPO) in mammalian cells, Gene, Vol. 199, 1997, pp. 293-301). Specifically, in the case of the L chain, a DNA sequence essential for efficient translation (Kozak, M., J., At least six nucleotides preceding the AUG initiator codon enhance translation in mammalian cells. J. Mol. Biol. 196, pp. 947-950, 1987), a signal peptide of a mouse IGKV (k chain variable region) gene, a V region of the L chain of an anti-CDH3 antibody, and human KC (k chain constant region) were aligned in this order, and restriction enzyme sites (NheI on the 5'-terminal side and EcoRI on the 3'-terminal side) were then added to the both termini. A chimeric H chain was produced in the same manner as described above. The thus produced artificial synthetic genes were cleaved with NheI and EcoRI, and the gene fragments were then inserted into the NheI and EcoRI sites of the expression vector pCAGGS, so as to obtain an expression vector pCAGGS-IGK for an anti-CDH3 chimeric antibody L chain, and an expression vector pCAGGS-IGH for an anti-CDH3 chimeric antibody H chain.

Example 10

Construction of Stable Expression Vector for Chimeric Anti-CDH3 Immunoglobulin

To allow a genetically modified antibody gene to express at a high level in CHO cells, an expression vector was constructed by ligating the gene to a CMV promoter sequence and introducing a dihydrofolate reductase (dhfr) gene having a poly(A) signal in the vector.

To produce a cell line capable of stably expressing and producing a chimeric antibody, a pCAGGS expression vector, into which a dhfr gene had been incorporated, was constructed. Specifically, a CMV promoter and a dgfr gene having a poly(A) signal were introduced into transient expression vectors pCAGGS-IGH and pCAGGS-IGK. A CMV promoter, a mouse dgfr gene having a Kozak sequence, and a SV40 poly(A) signal were each amplified according to a PCR method. Thereafter, a mixture of these DNA were connected with one another according to the PCR method, and at the same time, HindIII sites were added to both termini, so as to obtain a gene fragment HindIII-CMV promoter-Kozak-dhfr-poly(A)-HindIII. This fragment was inserted into the HindIII site of pCAGGS-IGH or pCAGGS-IGK to obtain pCAGGS-IGH-CMVp-dhfr-A and pCAGGS-IGK-CMVp-dhfr-A. These expression vectors enabled chimeric antibody expression with a CAG promoter, and dgfr gene expression with a CMV promoter, and thus, they were able to efficiently produce chimeric antibodies by utilizing gene amplification.

Example 11

Establishment of CHO Cell Line Capable of Producing Chimeric Anti-CDH3

CHO dhfr(-) cells (G. Urlaub et al., Isolation of Chinese hamster cell mutants deficient in dihydrofolate reductase activity, Proc. Natl. Acad. Sci. USA 77, pp. 4216-4220, 1980) were used in simultaneous transformation with two types of plasmids (wherein a plasmid was cleaved with PvuI in an ampicillin resistance gene to form linear plasmids from a cyclic plasmid), namely, with a pCAGGS-IGK-CMV-dhfr-A vector used for expression of a chimeric anti-CDH3 L chain and a pCAGGS-IGH-CMV-dhfr-A vector used for expression of a chimeric anti-CDH3 H chain. Electroporation was carried out using Amaxa manufactured by LONZA. DNA (0.002 mg/sample of each plasmid for the L chain and the H chain) was added to 0.1 mL of Amaxa electroporation CHO buffer containing 3×10e3 cells, and electric pulse was then given thereto.

The cells treated by electroporation were added to an Iscove's Modified Dulbecco Medium (IMDM), which contained 10% dialyzed FBS and did not contain HT (H: hypoxanthine; T: thymidine). Three days after the gene transfection, the medium was replaced with IMDM, which contained 10% dialyzed FBS and 2 mM L-glutamine, and did not contain HT. Thereafter, the transfected neo+ cells were selected with 1 mg/mL G418, and clones of a chimeric antibody production-positive cell line were obtained. Subsequently, gene amplification was carried out using the clones selected with G418. The gene was amplified in 2 rounds of methotrexate (MTX) (0.25 mM, 1 mM), and a cell line capable of producing approximately 50 to 100 mg of chimeric CDH3 antibody per liter could be established.

Example 12

Quantification of Chimeric Antibody by Enzyme-Linked Immunosorbent Assay (ELISA)

A culture supernatant of the transfected CHO cells was measured by ELISA, and it was confirmed that a chimeric antibody had been produced. To detect the chimeric antibody, a plate was coated with goat anti-human IgG (H+L) (which had previously been absorbed against mouse, rabbit, bovine, and mouse IgG) (COSMO BIO: AQI, Cat. No. A-110UD). After blocking, the culture supernatant obtained from CHO cells capable of producing anti-CDH3 chimeric antibody was subjected to serial dilution, and was then added to each well. After the plate had been subjected to incubation and washing, goat anti-human IgG (H+L) (which had previously been absorbed against mouse, rabbit, bovine, and mouse IgG)-HRP (COSMO BIO: AQI, Cat. No. A-110UD) was added to the plate. Following incubation and washing, a substrate buffer was added to the plate. Incubation was further carried out, the reaction was then terminated, and the absorbance at 450 nm was then measured. Purified human IgG was used as a standard.

Example 13

Binding Activity of Chimeric Antibody

An antibody having a combination of CDR sequences each shown in Table 2 was produced by the methods described in Examples 10 and 11, and the binding activity thereof was evaluated by flow cytometry.

Individual cell lines that would become reaction targets (CHO cells, CHO cells forcibly expressing CDH3, and NCI-H358 cell line that had been confirmed to express CDH3 at a high level) were each treated with 2 mM EDTA-PBS, so that they were removed from a culture plate, and the cells were then suspended in a FACS solution to a cell density of 1×10$^6$ cells/mL. This cell suspension was inoculated on a 96-well plate, resulting in an amount of 50 µL/well, and the purified chimeric antibody was then added to the plate to result in a concentration of 10 ug/mL, followed by performing a reaction at 4° C. for 60 minutes. Thereafter, the reaction mixture was washed with a FACS solution (150 µL/well) two times, and 4 µg/ml AlexaFlour488-labeled anti-human IgG/goat F(ab')$_2$ (Invitrogen) was then added. The obtained mixture was reacted at 4° C. for 30 minutes. Thereafter, the reaction mixture was washed with a FACS solution two times, and was then subjected to flow cytometry. As a result, the chimeric antibody was found to have strong reactivity with a CDH3-expressing cell line (FIG. 5).

TABLE 2

Combinations of antibody numbers and sequence numbers

| Antibody No. | CDR-H1 | CDR-H2 | CDR-H3 | CDR-L1 | CDR-L2 | CDR-L3 |
|---|---|---|---|---|---|---|
| 067-08C | SEQ ID NO. 48 | SEQ ID NO. 56 | SEQ ID NO. 65 | SEQ ID NO. 75 | SEQ ID NO. 82 | SEQ ID NO. 86 |
| 067-12C | SEQ ID NO. 51 | SEQ ID NO. 57 | SEQ ID NO. 67 | SEQ ID NO. 78 | SEQ ID NO. 83 | SEQ ID NO. 88 |
| 067-17C | SEQ ID NO. 49 | SEQ ID NO. 58 | SEQ ID NO. 68 | SEQ ID NO. 79 | SEQ ID NO. 82 | SEQ ID NO. 90 |
| 067-23C | SEQ ID NO. 50 | SEQ ID NO. 59 | SEQ ID NO. 69 | SEQ ID NO. 77 | SEQ ID NO. 83 | SEQ ID NO. 87 |
| 067-26C | SEQ ID NO. 52 | SEQ ID NO. 60 | SEQ ID NO. 70 | SEQ ID NO. 75 | SEQ ID NO. 82 | SEQ ID NO. 91 |
| 067-27C | SEQ ID NO. 53 | SEQ ID NO. 61 | SEQ ID NO. 71 | SEQ ID NO. 75 | SEQ ID NO. 82 | SEQ ID NO. 92 |
| 067-37C | SEQ ID NO. 54 | SEQ ID NO. 62 | SEQ ID NO. 72 | SEQ ID NO. 74 | SEQ ID NO. 81 | SEQ ID NO. 93 |
| 067-42C | SEQ ID NO. 55 | SEQ ID NO. 63 | SEQ ID NO. 73 | SEQ ID NO. 80 | SEQ ID NO. 85 | SEQ ID NO. 94 |
| 067-44C | SEQ ID NO. 49 | SEQ ID NO. 64 | SEQ ID NO. 66 | SEQ ID NO. 76 | SEQ ID NO. 84 | SEQ ID NO. 89 |

CDR-H1, H2 and H3 each indicate a CDR sequence constituting the H chain of each antibody. On the other hand, CDR-L1, L2 and L3 each indicate a CDR sequence constituting the L chain of each antibody.

Example 14

Synthesis of Drug

DM1 SMe (FIG. 6) was prepared as previously described in U.S. Pat. Nos. 5,208,020 and 6,333,410 B1.

Example 15

Preparation of Drug-Bound Antibody

1. Reduction Treatment of Bound Drug 0.78 mg of DM1 SMe dissolved in 300 uL of EtOH, 180 uL of a 50 mM potassium phosphate buffer (pH 7.5), and 20 uL of a TCEP Solution (Bond Breaker, Thermo Fisher Scientific K. K.) were mixed with one another, and the obtained mixture was then reacted in a nitrogen atmosphere at room temperature for 30 minutes or longer, so that the drug was reduced.

The reduced drug was purified by HPLC, and the solvent was then distilled away. The residue was dissolved in dimethylacetamide to a concentration of 10 mg/mL.

2. Preparation of Maleimidated Antibody

Sulfo-SMCC (PIERCE) was added to a 1 mg/mL anti-CDH3 chimeric antibody at a molar ratio of 30 : 1 or greater, and the obtained mixture was then reacted at 30° C. for 1 hour.

In order to remove an excessive amount of crosslinker, the reaction product was subjected to a desalination treatment with a desalination device that had been equilibrated with 50 mM potassium phosphate, 50 mM NaCl and 2 mM EDTA (pH 6.5) (ZebaSpinColumn, Thermo Fisher Scientific K. K.).

3. Modification of Antibody with Drug

A 1 mg/mL maleimidated anti-CDH3 chimeric antibody was reacted with a reducing agent that was 1.7-fold larger than the number of the bound maleimide groups in 50 mM potassium phosphate, 50 mM NaCl, and 2 mM EDTA (pH 6.5) at room temperature overnight. Subsequently, an excessive amount of drug was removed from the reaction mixture by gel filtration.

Example 16

Quantification of Amount of Drug Bound to Antibody

The number of drugs bound per antibody was determined by measuring the absorbance at 252 nm and 280 nm For the determination method, the absorption coefficients $\epsilon Ab_{280}=223,000$ $M^{-1}cm^{-1}$, $\epsilon Ab_{252}=82,510$ $M^{-1}cm^{-1}$, $\epsilon DM1_{280}=5,180$ $M^{-1}cm^{-1}$, and $\epsilon DM1_{252}=26,160$ $M^{-1}cm^{-1}$ described in a non-patent literature (Widdison, W. C., Wilhelm, S. D., Cavanagh, E. E., et al. (2006) Semisynthetic maytansine analogues for the targeted treatment of cancer. J. Med. Chem., 49, 4392-4408) were utilized.

Example 17

Cytotoxicity Test

The cytotoxicity and specificity of a drug-bound antibody were evaluated, using a cell growth measurement reagent (Dojindo Laboratories, Cell counting assay kit-8) in which WST-8 was used as a chromogenic substrate.

Specifically, a human breast cancer cell line HCC1954, in which high expression of CDH3 had been confirmed, was allowed to coexist with a drub-bound antibody (ADC) or with an antibody to which a drug was not bound (Naked) in any given amounts, and the obtained mixture was then incubated at 37° C. for 3 days in a 5% $CO_2$ environment. Thereafter, the cell growth measurement reagent was added to the resultant, and the obtained mixture was then left. Subsequently, the absorbance A450/620 was measured. The value of absorbance obtained from a well, to which only the cancer cell line had been added and no antibodies had been added, was set at 100%, and the obtained relative value was indicated as a cell survival percentage (FIG. 7). The antibody used in the figure was antibody No. 067-17C. With regard to ADC, the number of drugs introduced into a single antibody was calculated by the method described in Example 16. As a result, it was estimated that 4.05 drugs were introduced into a single molecule of antibody.

Example 18

Cytotoxicity Test (Comparison Among Individual Antibodies)

The cytotoxicity of the drug-bound antibody was evaluated using the obtained plurality of anti-CDH3 antibodies.

The measurement was carried out according to the method described in Example 17. That is to say, a human breast cancer cell line HCC1954 was allowed to coexist with a drug-bound antibody (ADC), and the obtained mixture was then incubated at 37° C. for 3 days in a 5% $CO_2$ environment. The concentration of the ADC during the incubation was set at 0.01 ug/mL. Thereafter, the cell growth measurement reagent was added to the resultant, and the obtained mixture was then left. Subsequently, the absorbance A450/620 was measured. The value of absorbance obtained from a well, to which only the cancer cell line had been added and no antibodies had been added, was set at 100%, and the obtained relative value was indicated as a cell survival percentage. The number of drugs introduced into a single molecule of antibody was calculated by the method described in Example 16 (Table 3).

As a negative control antibody, an antibody, which had been confirmed not to react with HCC1954, was used.

TABLE 3

| | Cell survival percentage of each antibody and number of drugs bound per antibody | |
|---|---|---|
| Antibody No. | Cell survival percentage (%) | Number of drugs bound per antibody |
| 067-08C | 81 | 3.1 |
| 067-26C | 82 | 3.6 |
| 067-37C | 94 | 5.9 |
| 067-42C | 75 | 5.4 |
| 067-44C | 56 | 7.2 |
| Negative control antibody | 101 | 6.7 |

Example 19

Animal Test

The effect of a drug-bound antibody to reduce tumor in vivo was confirmed using xenograft models into which the breast cancer cell line HCC1954 had been transplanted. For administration of the antibody, an anti-asialo GM1 antibody (WAKO 014-09801) was dissolved in 1 mL of Otsuka Distilled Water, and 4 mL of Otsuka Saline was then added to the solution to a total amount of 5 mL. Thereafter, 100 µL of the obtained solution per mouse was intraperitoneally administered to a mouse. HCC1954 was cultured in an RPMI1640 medium that contained 10% FBS, and the culture was then transplanted in an amount of $5 \times 10^6$ cells/mouse into the subcutis of the right abdominal wall of an SCID mouse (female, CLEA Japan, Inc.).

An in vivo test was carried out on 5 mice in each group, and the 15 mg/kg antibody was administered into the caudal vein of each mouse. Administration of the antibody was started when the mean tumor diameter became 100 to 150 mm³, and one week later, the same amount of antibody as described above was administered again. Thus, administration was carried out twice in total.

Antibodies with antibody numbers 067-12C, 067-23C and 067-27C, as shown in the figure, were used. With regard to ADC, the number of drugs introduced into a single antibody was calculated by the method described in Example 16. As a result, it was estimated that 3 to 4 drugs were introduced into a single molecule of antibody.

A change in the tumor size is shown in FIG. 8.

The invention claimed is:

1. An immune complex formed by binding a monoclonal antibody against CDH3 or a fragment thereof having CDH3 binding ability to a chemotherapeutic agent,
   wherein the monoclonal antibody against CDH3 or a fragment thereof having CDH3 binding ability is indirectly bound to the chemotherapeutic agent via a linker, wherein said linker is N-succinimidyl 4-(maleimidomethyl)cyclohexanecarboxylate (SMCC), and
   wherein said cytotoxic agent is DM1.

2. An immune complex formed by binding a monoclonal antibody against CDH3 or a fragment thereof having CDH3 binding ability to a chemotherapeutic agent,
   wherein the monoclonal antibody against CDH3 or a fragment thereof having CDH3 binding ability is indirectly bound to the chemotherapeutic agent via a linker, wherein said linker is selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), N-succinimidyl 4(2-pyridylthio) pentanoate (SPP), N-succinimidyl(4-iodoacetyl)aminobenzoate (SIAB), and N-succinimidyl (4-(2-pyridylthio)butanoate (SPDB), or said linker comprises val-cit or PABA,
   wherein said antibody comprises the amino acid sequences shown in SEQ ID NOs. 48, 56 and 65 as CDR-H1, CDR-H2 and CDR-H3, respectively, and comprises the amino acid sequences shown in SEQ ID NOs. 75, 82 and 86 as CDR-L1, CDR-L2 and CDR-L3, respectively.

3. An immune complex formed by binding a monoclonal antibody against CDH3 or a fragment thereof having CDH3 binding ability to a chemotherapeutic agent,
   wherein the monoclonal antibody against CDH3 or a fragment thereof having CDH3 binding ability is indirectly bound to the chemotherapeutic agent via a linker, wherein said linker is selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), N-succinimidyl 4(2-pyridylthio)pentanoate (SPP), N-succinimidyl(4-iodoacetyl)aminobenzoate (SIAB), and N-succinimidyl (4-(2-pyridylthio)butanoate (SPDB), or said linker comprises val-cit or PABA,
   wherein said antibody comprises the amino acid sequences shown in SEQ ID NOs. 52, 60 and 70 as CDR-H1, CDR-H2 and CDR-H3, respectively, and comprises the amino acid sequences shown in SEQ ID NOs. 75, 82 and 91 as CDR-L1, CDR-L2 and CDR-L3, respectively.

4. An immune complex formed by binding a monoclonal antibody against CDH3 or a fragment thereof having CDH3 binding ability to a chemotherapeutic agent,
   wherein the monoclonal antibody against CDH3 or a fragment thereof having CDH3 binding ability is indirectly bound to the chemotherapeutic agent via a linker, wherein said linker is selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), N-succinimidyl 4(2-pyridylthio)pentanoate (SPP), N-succinimidyl(4-iodoacetyl)aminobenzoate (SIAB), and N-succinimidyl (4-(2-pyridylthio)butanoate (SPDB), or said linker comprises val-cit or PABA,
   wherein said antibody comprises the amino acid sequences shown in SEQ ID NOs. 54, 62 and 72 as CDR-H1, CDR-H2 and CDR-H3, respectively, and comprises the amino acid sequences shown in SEQ ID NOs. 74, 81 and 93 as CDR-L1, CDR-L2 and CDR-L3, respectively.

5. An immune complex formed by binding a monoclonal antibody against CDH3 or a fragment thereof having CDH3 binding ability to a chemotherapeutic agent,
   wherein the monoclonal antibody against CDH3 or a fragment thereof having CDH3 binding ability is indirectly bound to the chemotherapeutic agent via a linker, wherein said linker is selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), N-succinimidyl 4(2-pyridylthio)pentanoate (SPP), N-succinimidyl(4-iodoacetyl)aminobenzoate (SIAB), and N-succinimidyl (4-(2-pyridylthio)butanoate (SPDB), or said linker comprises val-cit or PABA, wherein said antibody comprises the amino acid sequences shown in SEQ ID NOs. 55, 63 and 73 as CDR-H1, CDR-H2 and CDR-H3, respectively, and comprises the amino acid sequences shown in SEQ ID NOs. 80, 85 and 94 as CDR-L1, CDR-L2 and CDR-L3, respectively.

6. An immune complex formed by binding a monoclonal antibody against CDH3 or a fragment thereof having CDH3 binding ability to a chemotherapeutic agent, wherein the monoclonal antibody against CDH3 or a fragment thereof having CDH3 binding ability is indirectly bound to the chemotherapeutic agent via a linker, wherein said linker is selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), N-succinimidyl 4(2-pyridylthio)pentanoate (SPP), N-succinimidyl(4-iodoacetyl)aminobenzoate (SIAB), and N-succinimidyl (4-(2-pyridylthio)butanoate (SPDB), or said linker comprises val-cit or PABA, wherein said antibody comprises the amino acid sequences shown in SEQ ID NOs. 49, 64 and 66 as CDR-H1, CDR-H2 and CDR-H3, respectively, and comprises the amino acid sequences shown in SEQ ID NOs. 76, 84 and 89 as CDR-L1, CDR-L2 and CDR-L3, respectively.

7. An immune complex formed by binding a monoclonal antibody against CDH3 or a fragment thereof having CDH3 binding ability to a chemotherapeutic agent, wherein the monoclonal antibody against CDH3 or a fragment thereof having CDH3 binding ability is indirectly bound to the chemotherapeutic agent via a linker, wherein said linker is selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), N-succinimidyl 4(2-pyridylthio)pentanoate (SPP), N-succinimidyl(4-iodoacetyl)aminobenzoate (SIAB), and N-succinimidyl (4-(2-pyridylthio)butanoate (SPDB), or said linker comprises val-cit or PABA, wherein said antibody comprises the amino acid sequences shown in SEQ ID NOs. 49, 58 and 68 as CDR-H1, CDR-H2 and CDR-H3, respectively, and comprises the amino acid sequences shown in SEQ ID NOs. 79, 82 and 90 as CDR-L1, CDR-L2 and CDR-L3, respectively.

8. An immune complex formed by binding a monoclonal antibody against CDH3 or a fragment thereof having CDH3 binding ability to a chemotherapeutic agent, wherein the monoclonal antibody against CDH3 or a fragment thereof having CDH3 binding ability is indirectly bound to the chemotherapeutic agent via a linker, wherein said linker is selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), N-succinimidyl 4(2-pyridylthio)pentanoate (SPP), N-succinimidyl(4-iodoacetyl)aminobenzoate (SIAB), and N-succinimidyl (4-(2-pyridylthio)butanoate (SPDB), or said linker comprises val-cit or PABA, wherein said antibody comprises the amino acid sequences shown in SEQ ID NOs. 53, 61 and 71 as CDR-H1, CDR-H2 and CDR-H3, respectively, and comprises the amino acid sequences shown in SEQ ID NOs. 75, 82 and 92 as CDR-L1, CDR-L2 and CDR-L3, respectively.

9. An immune complex formed by binding a monoclonal antibody against CDH3 or a fragment thereof having CDH3 binding ability to a chemotherapeutic agent, wherein the monoclonal antibody against CDH3 or a fragment thereof having CDH3 binding ability is indirectly bound to the chemotherapeutic agent via a linker, wherein said linker is selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), N-succinimidyl 4(2-pyridylthio)pentanoate (SPP), N-succinimidyl(4-iodoacetyl)aminobenzoate (SIAB), and N-succinimidyl (4-(2-pyridylthio)butanoate (SPDB), or said linker comprises val-cit or PABA, wherein said antibody comprises the amino acid sequences shown in SEQ ID NOs. 51, 57 and 67 as CDR-H1, CDR-H2 and CDR-H3, respectively, and comprises the amino acid sequences shown in SEQ ID NOs. 78, 83 and 88 as CDR-L1, CDR-L2 and CDR-L3, respectively.

10. An immune complex formed by binding a monoclonal antibody against CDH3 or a fragment thereof having CDH3 binding ability to a chemotherapeutic agent, wherein the monoclonal antibody against CDH3 or a fragment thereof having CDH3 binding ability is indirectly bound to the chemotherapeutic agent via a linker, wherein said linker is selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), N-succinimidyl 4(2-pyridylthio)pentanoate (SPP), N-succinimidyl(4-iodoacetyl)aminobenzoate (SIAB), and N-succinimidyl (4-(2-pyridylthio)butanoate (SPDB), or said linker comprises val-cit or PABA, wherein said antibody comprises the amino acid sequences shown in SEQ ID NOs. 50, 59 and 69 as CDR-H1, CDR-H2 and CDR-H3, respectively, and comprises the amino acid sequences shown in SEQ ID NOs. 77, 83 and 87 as CDR-L1, CDR-L2 and CDR-L3, respectively.

11. The immune complex according to claim 1, wherein said antibody fragment having CDH3 binding ability is Fab, F(ab')$_2$, or scFv.

12. The immune complex according to claim 1, wherein 1 to 10 DM1s are bound to a single molecule of the antibody against CDH3 or the fragment thereof having CDH3 binding ability.

13. The immune complex according to claim 1, wherein 3 to 8 DM1s are bound to a single molecule of the antibody against CDH3 or the fragment thereof having CDH3 binding ability.

14. A pharmaceutical composition for treating cancer characterized by overexpression of CDH3, which comprises the immune complex according to claim 1.

15. The pharmaceutical composition according to claim 14, wherein said cancer is selected from among colorectal cancer, non-small-cell lung cancer, breast cancer, cancer of the head and neck, ovarian cancer, lung cancer, invasive bladder cancer, pancreatic cancer, metastatic brain tumor, thyroid cancer, squamous cell carcinoma of the head and neck, squamous cell carcinoma of the esophagus, squamous cell carcinoma of the lung, squamous cell carcinoma of the skin, melanoma, mammary cancer, pulmonary adenocarcinoma, squamous cell carcinoma of the uterine cervix, squamous cell carcinoma of the pancreas, squamous cell carcinoma of the colon, squamous cell carcinoma of the stomach, prostatic cancer, osteosarcoma, and soft tissue sarcoma.

\* \* \* \* \*